United States Patent [19]
Novotny et al.

[11] Patent Number: 5,252,326
[45] Date of Patent: Oct. 12, 1993

[54] FARNESENES AND RELATED SUBSTANCES FOR MOUSE CONTROL

[75] Inventors: Milos V. Novotny, Bloomington, Ind.; Scott D. Harvey, Richland, Wash.; Bozena Jemiolo, Bloomington, Ind.

[73] Assignee: Research Corporation Technologies, Inc., Tucson, Ariz.

[21] Appl. No.: 996,374

[22] Filed: Dec. 23, 1992

Related U.S. Application Data

[63] Continuation of Ser. No. 735,971, Jul. 25, 1991, abandoned, which is a continuation of Ser. No. 435,868, Nov. 13, 1989, abandoned.

[51] Int. Cl.$^5$ ............................................. A01N 25/00
[52] U.S. Cl. ..................................... 424/54; 514/762; 514/920
[58] Field of Search ................... 424/84; 514/762, 920

[56] References Cited

U.S. PATENT DOCUMENTS 4,209,529 6/1980 Tomiyama ........................... 424/312

OTHER PUBLICATIONS

Novotny et al, Science vol. 23P pp. 722-724, 1985.
Schwende et al, CA 104: 142428k 1986.
Harvey, Dissertational Abstracts Int. vol. 49/11-B p. 4780, Indiana University 1988.
Coppola, CA 105:165762z 1986.
Andreolini et al, CA 107:233886m 1987.
Cavill et al. (1967) a-Farnesene, DuFour's Gland Secretion In The Ant, *Tetrahedron Letters* 23: 2201-2205.
Murray et al. (1969) a-Farnesene: Isolation from the Natural Coating of Apples, *Aust. J. Chem.* 22: 197-204.
Bowers et al. (1972) Aphid Alarm Pheromone: Isolation, Identification, Synthesis, *Science* 177: 1121-1122.
Jones et al. (1973) The Effect of Urine on the Investigatory Behavior of Male Albino Mice, *Physiol. Behav.* 11: 35-38.
Picket et al. (1980) Composition of Aphid Alarm Pheromones, *J. Chem. Ecol.* 6: 349-360.
Gibson et al. (1983) Wild potato repels aphids by release of aphid alarm pheromone, *Nature* 302: 608-609.
Coppola, D. M. (1985) The Puberty Delay Pheromone and Population Regulation in the House Mouse, *Dissertation Abstracts Int.* 46: 1787-1918.
Novotny et al. (1986) Adrenal-Mediated Endogenous Metabolites Inhibit Puberty in Female Mice, *Science* 231: 722-725.
Schwende et al. (1986) Urinary Volatile Constituents of the House Mouse, *J. Chem. Ecol.* 12: 277-297.
Andreolini et al, (1987) Dynamics of excretion of urinary chemosignals in the house mouse (*Mus musculus*) during the natural estrous cycle, *Experientia* 43: 998-1002.

*Primary Examiner*—Frederick E. Waddell
*Assistant Examiner*—Russell Travers
*Attorney, Agent, or Firm*—Scully, Scott, Murphy & Presser

[57] ABSTRACT

The propagation of mouse population in a given area of actual or potential mice infestation is prevented as inhibited by treating such area with an effective amount of male mouse sesquiterpenic pheromone or a derivative thereof, wherein such pheromone has male mouse aversion signalling properties, and the pheromone is not used in the form of male mouse urine.

3 Claims, 14 Drawing Sheets

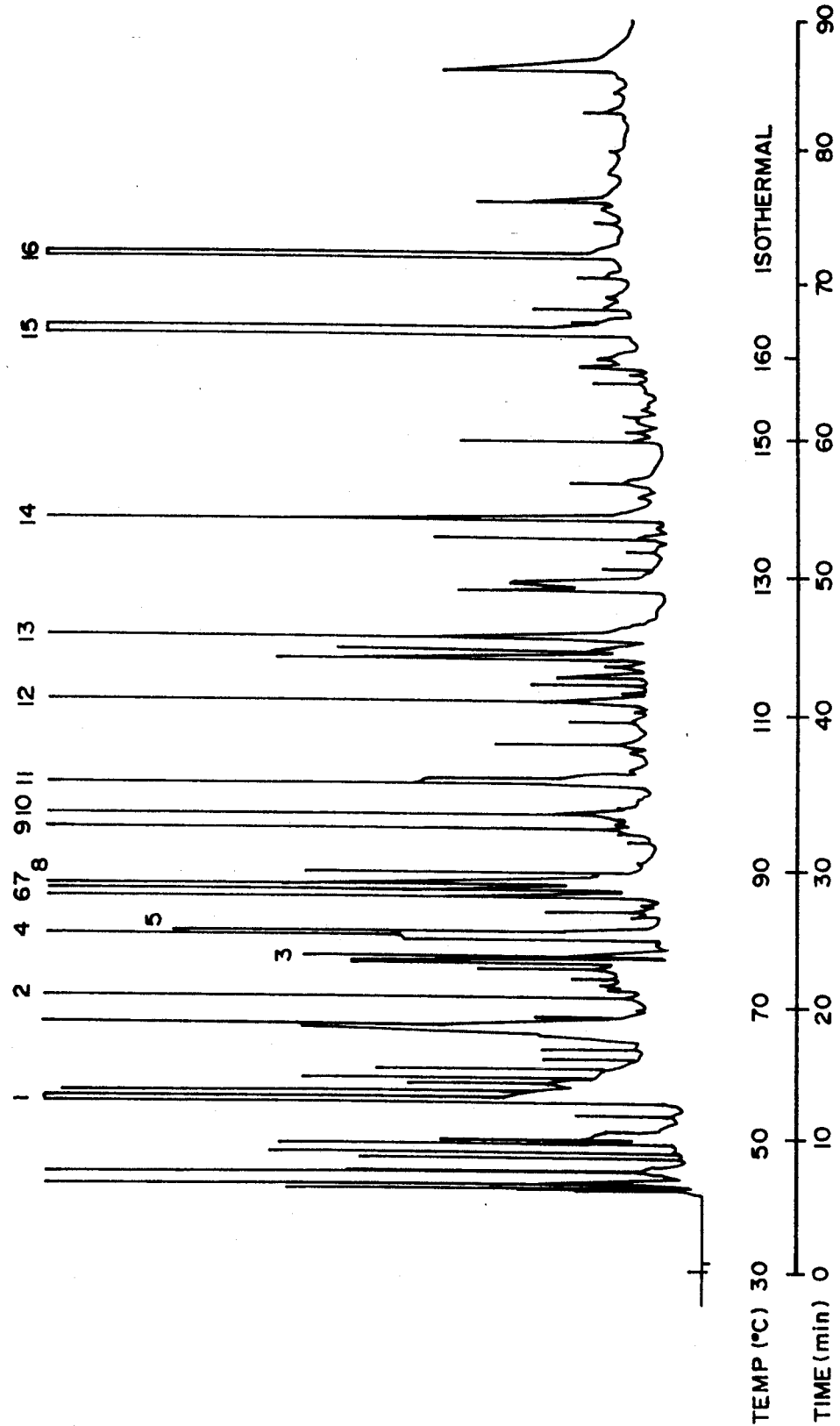

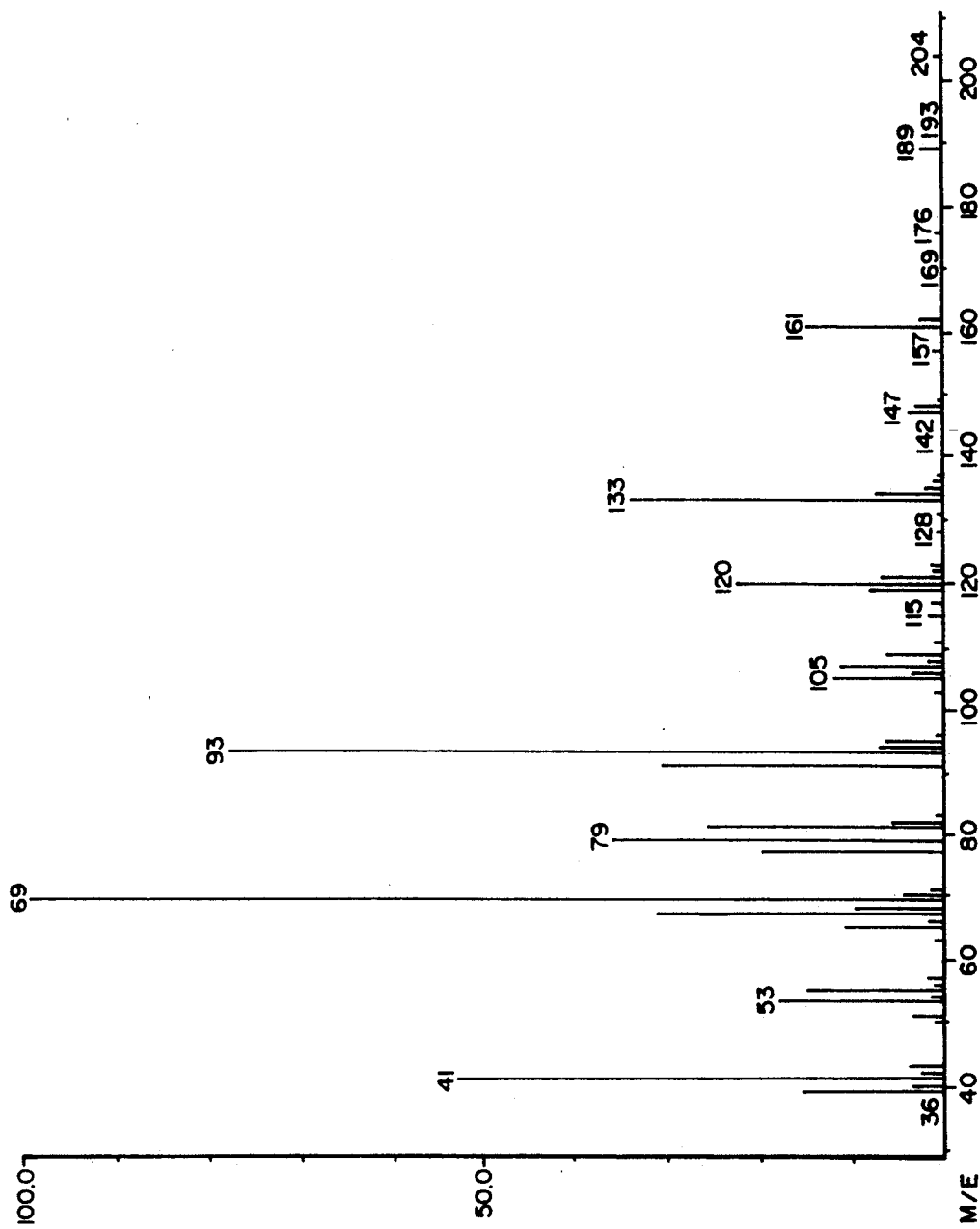

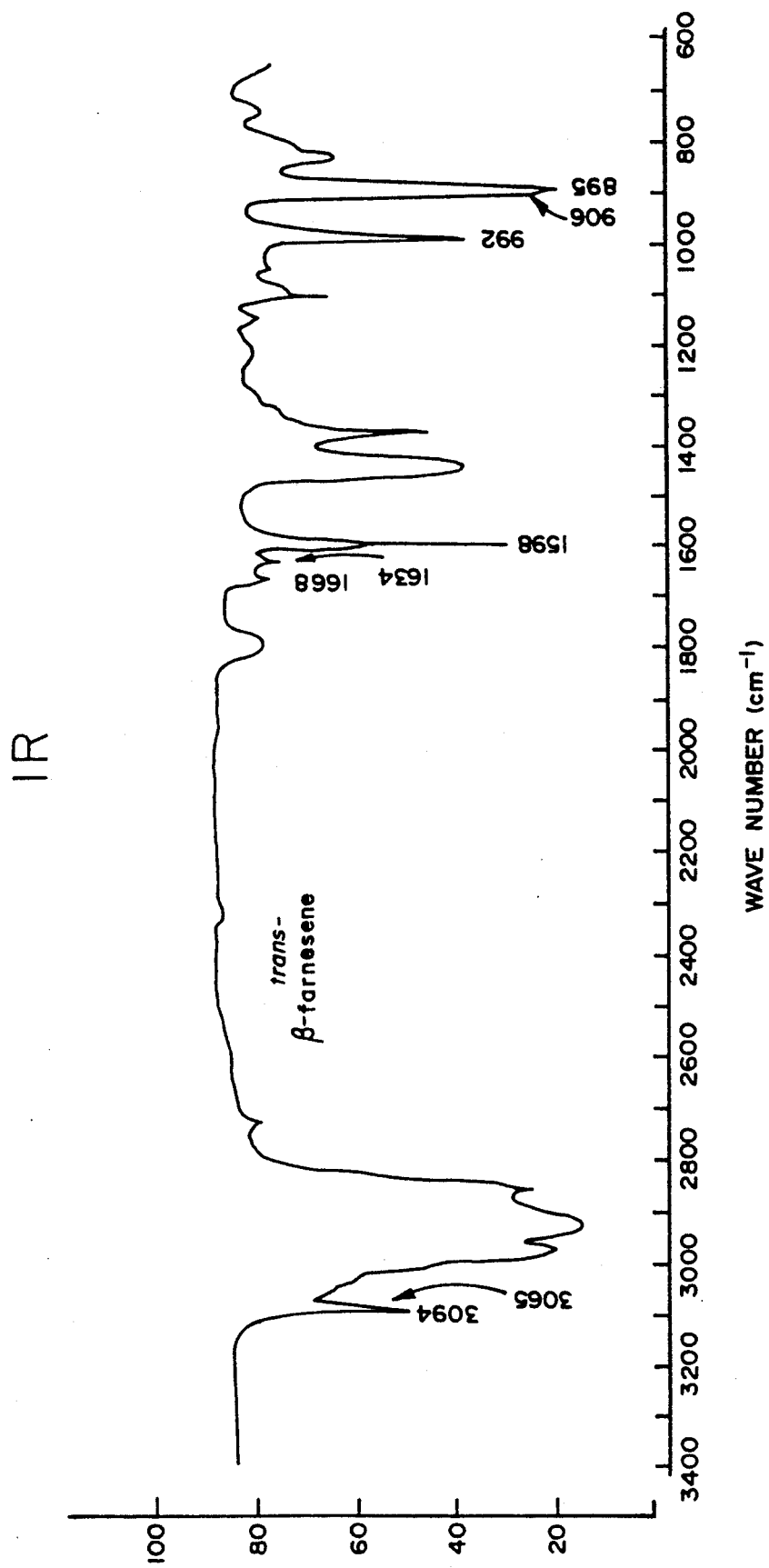

FARNESENES AND RELATED SUBSTANCES FOR MOUSE CONTROL

This is a continuation of copending application Ser. No. 735,971 filed on Jul. 25, 1991, now abandoned, which is a continuation of application Ser. No. 435,868, filed Nov. 13, 1989, now abandoned.

FIELD OF THE INVENTION

The present invention relates to the use of unique pheromonal substances of the preputial gland of male mice. In particular, this invention utilizes the farnesenes, which are major components of the preputial gland of the male mouse. Increased amounts of the product as shown here subordinate the male mouse's sexual responses. The present compounds, in synthetic or natural form, can substantially reduce the normal territorial and sexual investigatory activity of male mice. The present invention can thus be used, in various forms and combinations, to control mouse populations.

BACKGROUND OF THE INVENTION

Dominance-associated traits in male mammals such as aggression and territoriality have long been viewed as ecologically significant. It has been found that the dominant male mouse tends to sire more litters than the subordinate male mouse. Subordinate male mice occupy less desirable habitats, have a lower survival rate, and a lower reproductive potential than dominant male mice. In addition, there are numerous physiological attributes of subordination, such as poor spermatogenesis, decreased gonadal activity and abnormal adrenal function. The reproductive success of the dominant males has been previously and only partially explained by the fact that dominant males are known to deter subordinates from approaching "receptive" female mice. The dominant male produces an "aversion signal" that drives the subordinate male mouse away. This aversion signal is purportedly produced by secretions of the preputial gland of male mice. The preputial gland is believed to be a source of androgen-dependent sex-related pheromone. It is therefore desirable to utilize as mouse population controls, those chemical compounds which are responsible for the aversive signal since such compounds are capable of inhibiting the sexual activity of a male mouse and controlling the population growth of mice.

Mouse urine has been shown to be a rich source of olfactory cues which elicit changes in the reproductive behavior and physiology of recipient animals. The male urinary pheromones induce the pregnancy block, estrous synchronization, puberty acceleration, sexual attraction and interamale aggression and establish territory and social ranking. These pheromones are androgen-dependent and are not present in the urine of castrated mice. Social subordination is associated with suppressed gonadal function in male laboratory mice and brown lemmings, inhibited scent marking, suppressed ability of male urine to accelerate the onset of puberty in females and decreased ability of the urine to cause pregnancy blockage.

While it has long been assumed that urinary constituents, in a qualitative or quantitative sense, may signal the dominance of male mice, no chemical data had yet been reported on this subject prior to the present invention. However, the inventors have previously isolated urinary components under the control of the adrenal gland of the female mouse which have been effective in delaying the onset of puberty in female mice. These components are n-pentyl acetate, cis-2-penten-1-yl acetate and 2,5-dimethylpyrazine. levels of testosterone over subordinates and the dominant mouse's urine has an odor indicative of social status, the difference in the urinary volatile profiles of trained fighter males and subordinate males was then investigated. Several different pheromones were thoroughly investigated.

The first mouse pheromone effect to be thoroughly described by the present inventors was the promotion of inter-male aggression by dehydro-exo-brevicomin and 2-(sec-butyl)-4,5-dihydrothiazole. After detailed studies of the behavioral activity of these two compounds, it was discovered that they elicit vigorous and persistent antagonistic behavior from castrated male mice. The response provided by these two compounds is statistically indistinguishable from that found in normal male mice. The fact that these compounds are not active when spiked into water suggests that other compounds may be involved. Such additional compounds may simply provide a familiar and meaningful context in which to perceive the pheromones. 2-sec-butyl-4,5-dihydrothiazole and 3,4-dehydro-exo-brevicomin also account for at least two more pheromone effects. These compounds act synergistically to attract female mice when presented in the context of castrated male urine. It was also found that these two compounds were capable of increasing the frequency of estrus in females which were caged in high-density population conditions. For this pheromone effect, the two compounds spiked into water were sufficient to elicit a response. The effect of the synthetic compounds was similar to that of normal male urine, except that the response was somewhat attenuated when tested on females living under low-density population conditions.

The majority of work done on the preputial gland has involved the chemical characterization of lipids produced by this gland and their ramifications as related to dermatology. The preputial gland of the mouse is a specialized, testosterone-dependent sebaceous gland which is easily isolated as a pure preparation. Since obtaining a pure preparation of sebaceous glands from skin is difficult, preputial glands have been used as a model system for investigating the biochemistry of sebaceous glands. The primary orientation of past investigations have not emphasized the chemical signaling (i.e., "aversive signal") function of this gland.

Studies reveal that the chemical composition of preputial gland lipids depends on the age and sex of mice. Analysis of glands from immature male mice indicated that sterol esters and triglycerides were the principal lipids present. Acetates account for 5% of lipids in the preputial glands from male mice and 1% of the lipids in glands from female mice. Further investigation and chemical characterization of the semivolatile components of the preputial gland is described in the present invention.

Two sesquiterpenic constituents of the preputial gland of the mouse have been isolated and shown to be responsible for the "aversive signal" resulting in significantly discouraging prolonged territorial and sexual investigation by male mice, according to the present invention. These two constituents, which are the territorial markers used by dominant male mice, have been identified as E,E-alpha-farnesene and E-beta-farnesene.

Previously, alpha- and beta-farnesene have been shown to be present as naturally occuring compounds in various plant materials. The farnesyl pyrophosphate is a well-known key intermediate in the biosynthesis of steroids. Alpha-farnesene was isolated by Murray (*Aust J. Chem.*, 22: 197, 1969) from the natural coating of apples. Spectroscopic studies verified the trans configuration of the double bond at the 3,4 position but the author was unable to verify the geometry at the 6,7 position. Later studies by Anet (*Aust. J. Chem.*, 23: 2101, 1970) showed the apple farnesene to be the E,E-alpha-farnesene. Alpha-farnesene has also been isolated from pears and quinces. Z,E-alpha-farnesene has been isolated from the oil of *Perrila frutscens f. viridis*, an Asiatic mint, by Sakai and Hirose, *Bull.* Chem. Japan, 42: 3615, 1969. These authors also isolated the cis and trans allofarnesenes from the sesquiterpene fraction of this oil. Analysis of the essential oil of hops revealed the presence of both alpha- and beta-farnesene. As already indicated, trans-beta farnesene has also been isolated from the oil of chamomile.

The farnesenes have been isolated from several animal sources. The springbok releases an exudate from its dorsal gland which is thought to function as a conspecific alarm signal. Among the compounds found in this secretion are alpha- and beta-farnesenes. Male Mediterranean fruit flies release a volatile pheromone which attracts and excites female flies. Baker, et al. (*J. Chem. Soc., Chem. Commun.*, 12: 842, 1985) identified nine compounds from the anal ampoule of male flies, of which E,E-alpha-farnesene is the major component.

A large body of evidence illustrates that the farnesenes are utilized by certain insects as pheromones. Ants produce a trail pheromone which is secreted by Dufour's gland. Initial studies showed that this gland's secretion was homogeneous and identical to the alpha-farnesene found in the coating of apple (see, e.g., Cavill, et al. *Tetrahedron Lett.*, 23: 2201, 1967; Murray, supra). More detailed studies analyzing whole-worker extracts of ants isolated four fractions which exhibit trail-following activity. The major active component was identified as Z,E-alpha-farnesene. E,E-alpha-farnesene was found in lower concentrations and also showed activity. The third and fourth active fractions were tentatively identified as homosesquiterpenes having the structures of Z,Z- and Z,E-3,4,7,11-tetramethyl-1,3,6,10-dodecatetrene. Vander Meer, et al. (*Tetrahedron Lett.*, 22: 1651, 1981) tested all six alpha- and beta-farnesene isomers and found Z,Z-alpha, E,Z-alpha-, E-beta-, and Z-beta-farnesenes inactive.

Farnesenes are also utilized as pheromones by aphids. When presented with a predator, the aphids release an alarm pheromone identified as E-beta-farnesene, from their cornicles which causes conspecifics to drop from their feeding spots, thus escaping the predator. After dropping from the plant, the aphid remains immobilized for a short period. This post-exposure quiescence is sometimes referred to as "feigning thanatosis". E-beta-farnesene shows biological activity in at least ten aphid species, making this the most interspecially active pheromone known. While studying the volatile components of *Myzus persicae*, Pickett and Griffiths (*J Chem. Ecol.*, 6: 349, 1980) also found small amounts of E,E- and Z,E-alpha-farnesene. These alpha-farnesenes do not elicit an alarm response in the aphids; however, they may potentiate the effects of E-beta-farnesene.

The biological precursors for alpha- and beta-farnesene, in the preputial gland, are ocimene and myrcene. It is well established that geranyl pyrophosphate condenses with the five-carbon isopentenyl pyrophosphate to form farnesyl pyrophosphate. The farnesyl pyrophosphate is a key intermediate in steroid biosynthesis. It appears that an analogous metabolic pathway is present in the preputial gland of the male mouse; myrcene or ocimene units may condense with geranyl pyrophosphate to form E-beta-farnesene and E,E-alpha-farnesene, respectively. Absence of the farnesenes from bladder urine and identification of these compounds in the preputial glands identifies this gland as the site of secretion of these compounds. Additionally, identification of the biological precursors of the farnesenes, myrcene and ocimene, implicates this gland as the site of biosynthesis of the farnesenes. The chemical structures of myrcene, ocimene, E,E-alpha-farnesene and E-beta-farnesene are represented below.

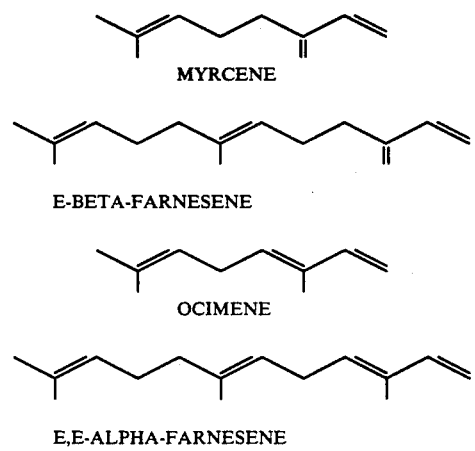

MYRCENE

E-BETA-FARNESENE

OCIMENE

E,E-ALPHA-FARNESENE

SUMMARY OF THE INVENTION

Accordingly, one object of the present invention is to provide a method for population control in mice (Mus domesticus).

A further object of the present invention is to provide new products for use in population control of mice.

Another object of the present invention is to provide a composition or formulation for use in mouse control as a repellant or inhibitor of sexual behavior in mice.

These and other objects of the present invention are achieved by providing a protocol which permits the isolation or synthesis of certain male mouse pheromones, the farnesenes, and utilizing these products in an appropriate carrier system for the control of mouse populations. The male mouse pheromones, e.g., farnesenes or derivatives thereof capable of effecting the "aversive" signal in mice, are provided in an appropriate medium, e.g., water or other conventional solid, semi-solid or liquid carriers, in order to mimic their natural occurrence in mouse urine. These compositions can be used to significantly inhibit territorial and sexual investigations by male mice, enabling population control of mice.

The present invention specifically contemplates a mouse repellant composition which includes an effective amount of a male mouse pheromone derived from the preputial gland of the mouse, the farnesenes, and a conventional carrier or delivery system. These compositions can be employed in a method to control mouse populations by inhibiting the investigatory and colonizing activities of male mice. Exposure of the present composition to male mice in effective amounts for a sufficient time deters the sexual behavior of male mice in a manner which substantially inhibits and terminates mouse reproduction.

DETAILED DESCRIPTION OF THE INVENTION

Figure 1B:
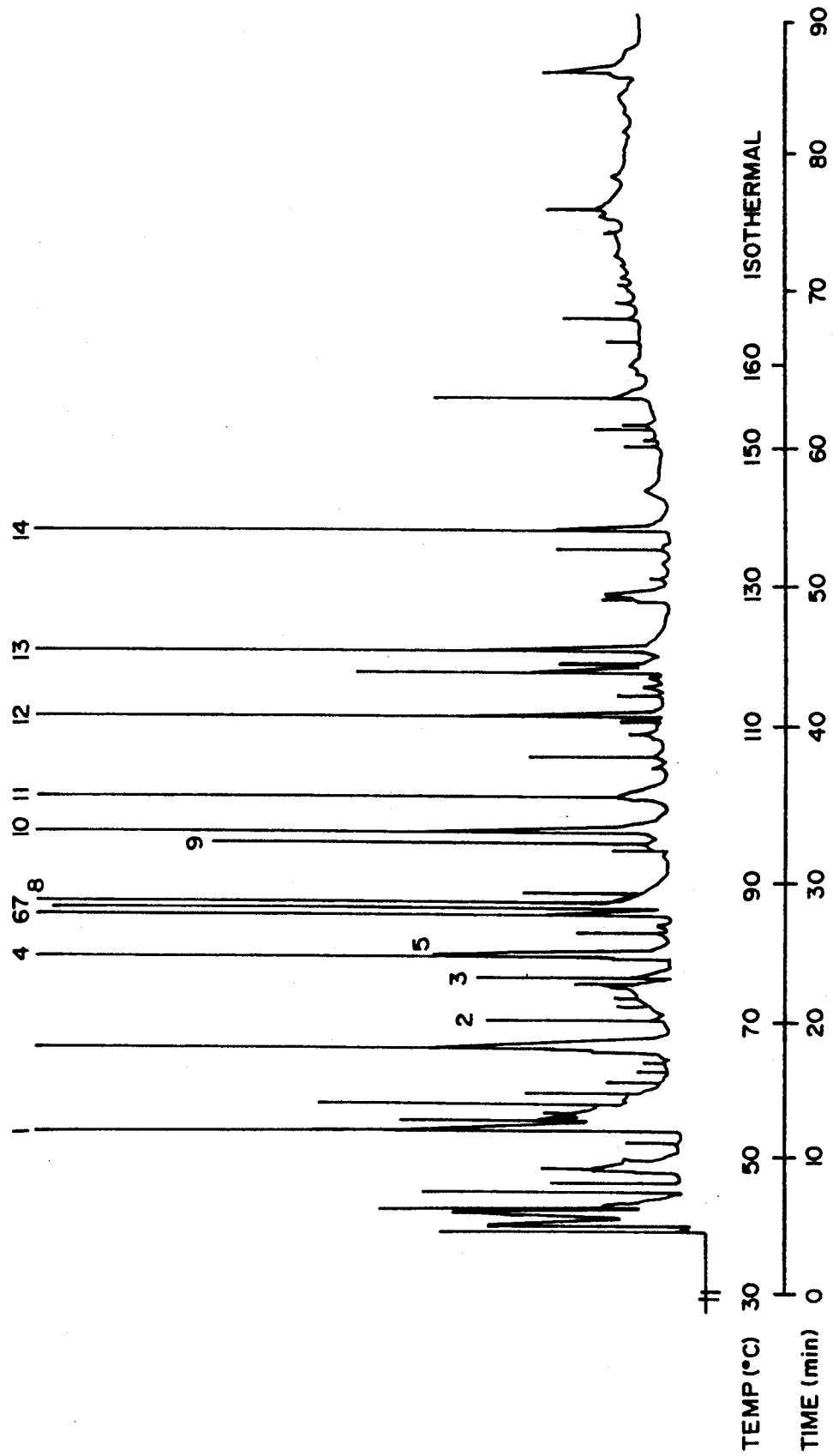
FIG. 1 is a representation of the capillary gas chromatograms (substance profiles) of the volatiles from externally voided dominant male mouse urine (FIG. 1a) from bladder urine of a subordinate male mouse (FIG. 1b).

The present invention contemplates a new method for population control in mice using certain male mouse pheromones of the preputial gland, e.g., alpha- and beta-farnesene and their derivatives. It has been found by the present inventors that these pheromones are the essence of the normal dominance signaling to mice via urine marking and are capable of substantially reducing the normal investigatory activity of the male mouse by having a substantially aversive effect on the subordinate male mouse.

In particular, the present invention contemplates a method utilizing a composition comprising an effective amount of natural or synthetic male mouse pheromones of the preputial gland as a mouse repellant. While the use of pheromonal substances is well detailed in insect control, it was unexpected that such substances could be similarly found in mammals, and in particular, that it could readily be adapted to mouse control. Since farnesenes are not harmful to humans, compositions containing an effective amount of these compounds can be used to control mice population explosions around grain storages, food supplies, or in homes and businesses by inhibiting exploration and colonization by mice.

The present invention, therefore, contemplates new compositions of these mouse pheromones. More specifically, the present invention is directed to a composition containing an amount of the mouse pheromone effective to mimic the "aversive" effect in nature. The pheromones can be used or delivered as such, or in a conventional carrier or delivery system permitting their exposure and gradual release to the surrounding atmosphere.

The pheromones of the present invention are certain male mouse pheromones of the preputial gland, the farnesenes. The conventional carriers of the present invention are, for example, natural or synthetic organic or inorganic materials, solvents or suspension materials.

The delivery systems useful in the present system may be, for example, solids or other matrices or mechanical devices or aerosol sprays.

The amounts of the active pheromone useful in the present composition ranges from about 0.01% to about 95% of the total composition and preferably between 5% and 25% of the total composition.

Mice are known to exhibit territoriality, i.e., dominance and aggressiveness, which is controlled by chemical messengers, specifically, by androgen levels. Dominant mice have higher androgen levels, are more aggressive, and their urine exerts an "aversive" effect inhibiting exploratory activity by other mice (both subordinate and dominant). The surprising advantages of the present invention are two-fold: First of all, the chemical substances, i.e., the farnesenes, responsible for this "aversive" pheromonal effect have never previously been characterized in this context. Secondly, this effect has never been reproduced. The compositions of the present invention are intended to mimic the effects of dominant male mouse urine and thus, act as a mouse repellant and inhibitor of mouse exploratory behavior. The farnesenes retain their ability to repel mice when tested in water alone.

The male mouse pheromones of the preputial gland, particularly, alpha- and beta-farnesenes and their derivatives, can be isolated from the preputial gland of the dominant male mouse.

This is done by extracting the sebum contents of the preputial gland, and concentrating the resulting solution and analyzing this solution by chromatography in order to identify the farnesene components.

The pheromones used in the present invention, e.g., farnesenes, whether present in water or in other matrices, are capable of rendering a stimulus to the male mouse which is behaviorally similar to the urine of dominant males at the amounts which are useful in the present composition. This is synonymous with the "aversion signal" produced by dominant males. A composition containing synthetically produced or naturally produced farnesenes in various forms can be used as described herein to reduce the normal investigatory activity of the male mice and control propagation of mouse populations. The alpha and beta farnesenes can be used singularly or in combination in the appropriate composition as described below. The farnesene is present in the composition in a concentration of from about 1 ppm (part per million) to about 50 ppm, v/v, each.

The following previously-isolated components of the adrenal gland of the female mouse have been shown to be effective in delaying the onset of puberty in female mice: n-pentyl acetate, cis-2-penten-1-yl acetate and 2,5-dimethylpyrazine. The present invention also contemplates a composition which contains the farnesenes in combination with one or more of the above components in concentrations mimicking their natural occurrence in female mouse urine. The combinations particularly contemplated in the present invention include one or both of the farnesenes and 2,5-dimethylpyrazine; one or both of the farnesenes and n-pentyl acetate and cis-2-penten-1-yl acetate; or one or both of the farnesenes and n-pentyl acetate, cis-2-penten-1-yl acetate and 2,5-dimethylpyrazine. Each of the acetates is present in the composition at a concentration of about 1 to 10 ppm, v/v, each. The 2,5-dimethylpyrazine is present at a concentration of 20 to 80 ppm, v/v, each.

The compositions of the present invention can be prepared in a variety of forms adapted to the chosen method of dispersal. In practical use, the compounds of the subject invention are rarely used alone. Most often they form part of compositions. The compositions, which can be useful as repellents for mice and/or as inhibitors of the investigatory and colonizing abilities of male mice, contain as the active substance a compound according to the invention as described previously, in association with solid, semi-solid, or liquid carriers which are environmentally acceptable. Conventional inert carriers can especially be used. The term "carrier", in the present description, denotes a natural or synthetic organic or inorganic material, with which the active substance is combined in order to facilitate its application in the prescribed places, i.e., those places where mice live, breed, or are generally troublesome. Therefore, this carrier is generally inert and it must be environmentally acceptable, especially in the treated areas.

The compositions can thus be dispersed in a carrier matrix which will release the active ingredient slowly into the prescribed area. The carrier may be solid (talos, kaolin, diatomaceous earth, natural or synthetic silicates, silica, resins, waxes, etc.) or liquid (alcohols, ketones, petroleum fractions, aromatic or paraffinic hydrocarbons, liquified gases, etc.).

The compositions may be formulated as dusting powders or granules comprising the active ingredient and a solid diluent or carrier, for example, fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler.

The active ingredient can also be impregnated into polymeric matrices which allow the slow release of the active ingredient. Some polymers useful for this are celluloses, polystyrenes, polyamides, polyesters, and the like. These plastic polymers are readily moldable into many shapes and sizes.

The above formulations are usually prepared so as to contain from about 0.01% to 95% of active compound, and about 5.0% to 99.8% of inert carrier and about 0.1% to 20% of other additives such as stabilizers or antioxidants and perfumes.

Another method of dispersion of the active compounds is impregnating a semi-solid matrix that will evaporate slowly thereby allowing the active compound to be released slowly. A solution of active compound in a suitable volatile solvent may also be used to provide a slow release of the active ingredient. This method could employ a sealed container with a wick-type of material within the liquid or a container which allows a controlled release of the solution, e.g., dripping onto a sponge-like material.

The compositions could also be employed in conjunction with a mechanical device for controlling the release of the active ingredient or a solution containing the active ingredient, for example, a solution containing an active compound in an aerosol container could be controlled by a timer to release the solution at prescribed intervals.

Suitable organic solvents are ethylene dichloride, isopropyl alcohol, polyethylene glycol, propylene glycol, diacetone alcohol, toluene, kerosene, methylnaphthalene, the xylenes, ethers, trichloroethylene, furfuryl alcohol, tetrahydrofurfuryl alcohol, glycol ethers (e.g., 2-ethoxyethanol and 2-butoxyethanol), mineral oil, and the like.

The compositions to be used as sprays may also be in the form of aerosols wherein the formulation is held in a container under pressure in the presence of a propellant, e.g., fluorotrichloromethane, dichlorodifluoromethane, or a hydrocarbon.

The active ingredient may be combined with a food source as bait. The types of foods, e.g., grains such as oats, wheat, corn, etc. can be treated with one of the compositions described above or the active ingredient alone. The best baits are well-known to the pest control professional.

The compositions of the invention can also contain stabilizers (antioxidants) and/or perfumes. Antioxidants include butylated hydroxytoluene (BHT), butylatedhydroxyarisol (BHA), dialkylthiopropionates, xanthates and the like. These can be present in about 0.1 to 5% by weight.

The perfumes can be added to give the compositions a pleasing odor. Some perfumes are oil of wintergreen, peppermint oil, citrus oils, and the like.

The following examples further assist in detailing the subject invention without limiting its scope.

EXAMPLES

The ICR/Alb albino mice used in the experiments were initially mated pairs purchased from Ward's Natural Science Establishment, Inc., Rochester, N.Y., which were then randomly bred closed-colony. All animals were maintained at $21 \pm 0.2°$ C., 50–70% humidity and a 12-hr light/12-hr dark daily regime (lights on at 0600 h).

EXAMPLE I

Social Rank Test

Prior to the social rank test, each male mouse was maintained in social isolation from 25 days of age. At the time of the experiment, the animals were 90–100 days of age. The control urine (1 ml) was collected from each male prior to beginning the rank test. Next, dominance or subordinance was established by pairing two males in a neutral arena for 10 minutes on each of 10 consecutive days. Males were originally paired so that neither male weighed over 2 g more than his partner. An animal was classified as dominant if its daily chase-attack score was significantly higher (Chi-square test; employing a 0.01 confidence interval) than that of the other member of the pair. Only males displaying a stable dominant-subordinate relationship during the 10 ranking tests were used. Eleven dominant and eleven subordinate males served as urine donors.

On the first day after completion of the social test, the first collection (collection 1) of urine from dominant and subordinate males took place. After first collection, the animals were kept in the home cage, undisturbed for the next six days. The second collection (collection 2) took place seven days after the social rank test was finished. One milliliter of urine was collected from each dominant and subordinate male during both collection periods. Two dominants and two subordinates served as bladder urine donors. Urine was collected directly from the bladder using needle and syringe. Two samples of bladder urine (1 ml of each) from dominant and subordinate males were analyzed. Subsequently, all tested animals were sacrificed, and the body, adrenal and preputial glands, the seminal vesicle plus coagulating glands and testes were dissected out and weighed.

Urine samples were also collected from immature and castrated males, as well as the castrates with testosterone. Three 1-ml urine samples were collected from twenty-one immature males when they were 21 days of age. In addition, nine immature males were castrated and housed in a group of three per cage until they reached the age of 90 days. At this time, three 1-ml samples of castrate urine were collected over three consecutive days. Four additional 21-day old males were castrated and housed in a group of two per cage. At the age of 90 days, a testosterone capsule (4 mm in size) was implanted in each animal. Ten days later, 4 ml of urine was collected from these testosterone-treated animals.

For a single chromatographic analysis, 1-ml urine samples were used. The number of chromatographic analyses for each type of urine corresponded with the number of milliliters for collected urine.

All urine samples were collected on a block of dry ice and immediately stored at $-20°$ C. Each collection period lasted six hours and started the same time each day, i.e., from 0900 to 1500 h.

The urinary volatiles of all the investigated samples were analyzed by capillary gas chromatography and identified by combined capillary gas chromatography/mass spectrometry.

The capillary gas chromatograms shown in FIG. 1 represent the substance profiles obtained from externally voided urine of dominant male mice and urine at a subordinate male bladder. The list of compounds identified in these profiles is provided in Table 1. Sixteen volatiles exhibited statistically significant ($p<0.02$) changes in concentration, depending on the social status of the animals or their endocrinological conditions. These volatile compounds have been subsequently identified as various dihydrofurans, ketones, acetates, dehydro-exo-brevicomin,2-(sec-butyl)-4,5-dihydrothiazole and the sesquiterpenes, alpha- and beta-farnesene.

Figure 2A:
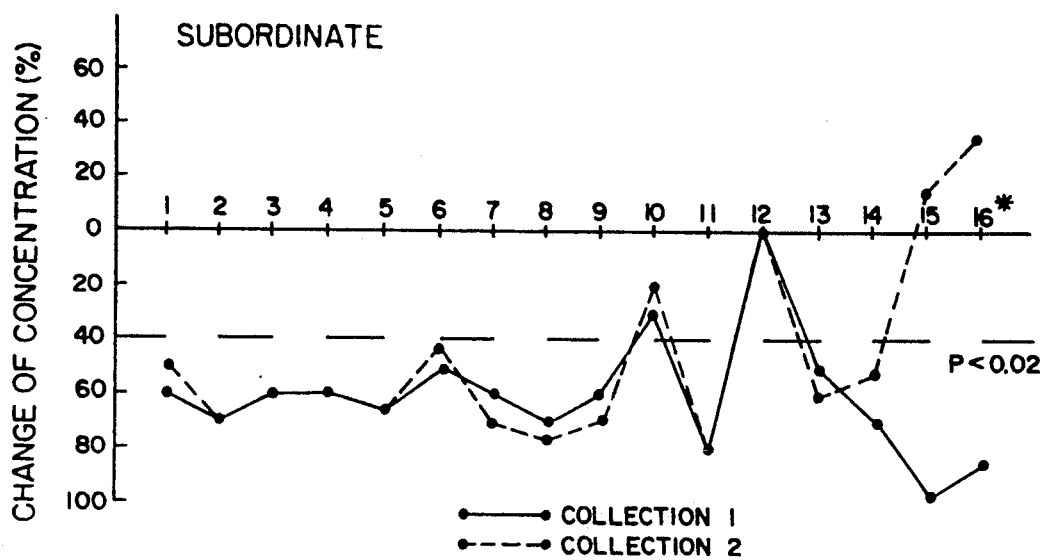
FIG. 2 is a graphical representation of the change in concentration of volatiles in subordinate (FIG. 2a) and dominant mouse (FIG. 2b) externally voided urine due to the social rank test.

As seen in FIG. 2a, the concentration of all selected dihydrofurans, ketones (except peak 10) and acetates are drastically decreased in the urine of subordinates collected immediately after social rank test (collection 1). Maintenance of all these volatiles at very low concentrations was still observed in the urines collected a week after the social rank test was completed (collection 2).

Figure 2B:
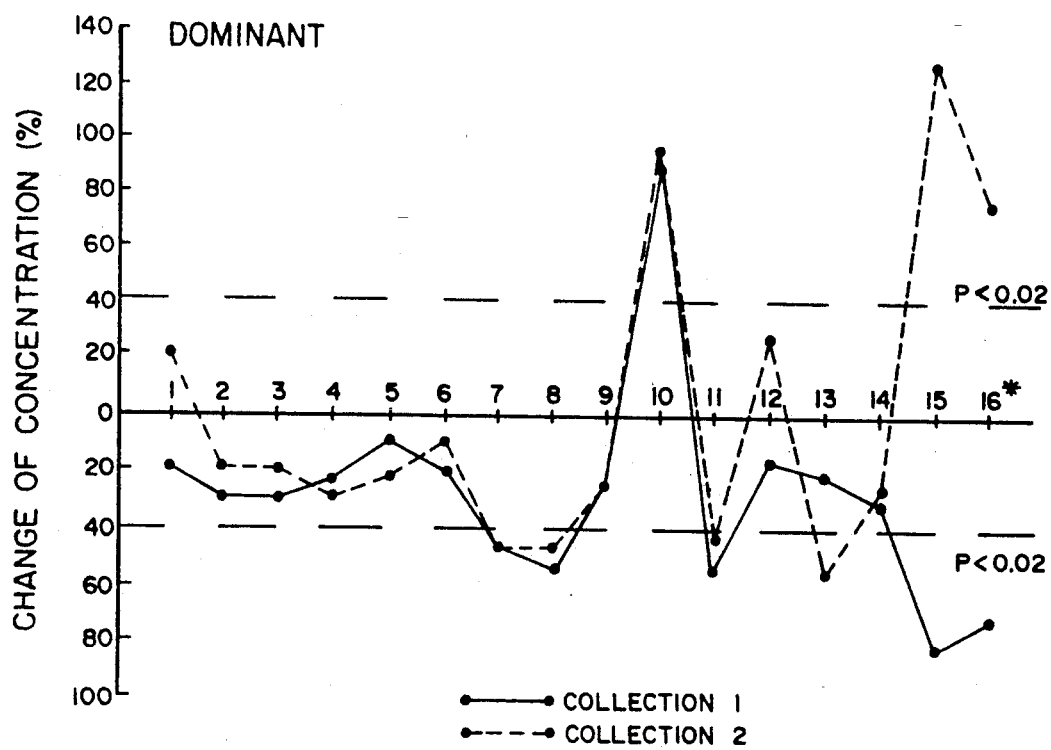

Urine of dominant males contained the dihydrofurans and acetates in concentrations similar to control animals regardless of the time of collection (FIG. 2b). A significant decrease of urinary ketones was observed only for peaks 7, 8, and 11, during either the first or second collection. While peak 10 exhibited no change of concentration in subordinate urine, it showed a trend to increase its level in dominant urine during both periods of collection.

The concentrations of alpha- and beta-farnesene dropped significantly in both dominant and subordinate urine immediately after the social rank test (collection 1; FIG. 2a and 2b). Only in dominant urine obtained during the second collection did both sesquiterpenes show a dramatic increase in concentration when compared to control and subordinate animals (FIG. 2a and 2b).

Social status of the males did not influence the dehydro-exo-brevicomin concentration (FIG. 2a and 2b). However, the concentration of 2-(sec-butyl)-4,5-dihydrothiazole dropped significantly in the urine of subordinates during both collection periods (FIG. 2a). The low level of this substance in dominant male urine was not found till some time after the social rank test (FIG. 2b).

The detailed chemical investigations of urine from immature, adult intact, castrated males and castrated animals with testosterone implants reveal the importance of four of the selected volatile compounds with respect to hormonal function and social status of mice. These compounds are alpha-farnesene, beta-farnesene, dehydro-exo-brevicomin and 2-(sec-butyl)-4,5-dihydrothiazole (Table 2). None of these four compounds were observed in the urine of immature males. The remaining twelve out of sixteen selected compounds were always present in the urine from immature males, although at a low concentration. Castration reduced the levels of alpha- and beta-farnesene and completely depressed the concentrations of dehydro-exo-brevicomin and 2-(sec-butyl)-4,5-dihydrothiazole (Table 2). Ten days of testosterone treatment reduced the levels of both sesquiterpenes in the male urine, when compared to intact and castrated males, and partially restored the presence of dehydro-exo-brevicomin and 2-(sec-butyl)-4,5-dihydrothiazole (Table 2). The decrease of alpha- and beta-farnesene to a value below 1.0 (arbitrary units) was previously observed only for subordinate male urine at collection 1 (alpha-farnesene=0.4, and beta-farnesene=0.7±0.4).

Dehydro-exo-brevicomin was found at a similar concentration in both dominant and subordinate bladder urines; however, at a significantly higher level when compared to control, excreted urine. 2-(sec-butyl)-dihydro thiazole was present in the bladder urine of subordinate and dominant males at concentrations comparable to those found in excreted urine, but dominant bladder urine contained significantly more 2-(sec-butyl)-4,5-dihydrothiazole than did the bladder urine of subordinates (Table 2).

There were no significant differences in the body weights and the weights of seminal vesicles plus coagulation glands between control, dominant and subordinate males (Table 3). In marked contrast, the dominant animals had significantly greater preputial glands when compared to subordinate and control (castrated) males. Only subordinate males had significantly larger adrenal glands and smaller testes when compared to control and dominant males (Table 3).

Figure 3A:
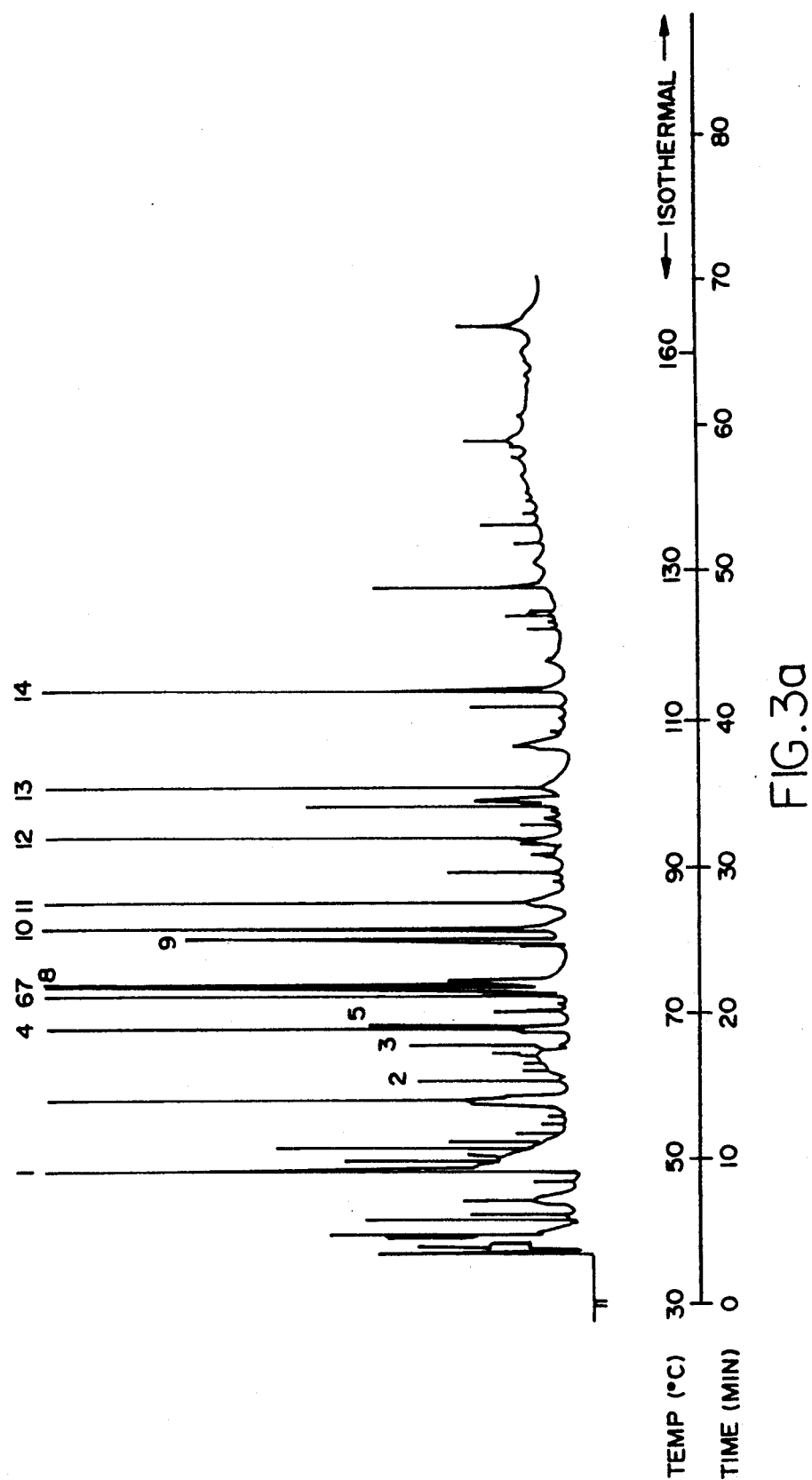
FIG. 3 is a comparison of the representative chromatograms of the volatiles from subordinate mouse bladder urine (FIG. 3a) and the volatiles from the dominant mouse preputial gland (FIG. 3b).
Figure 3B:
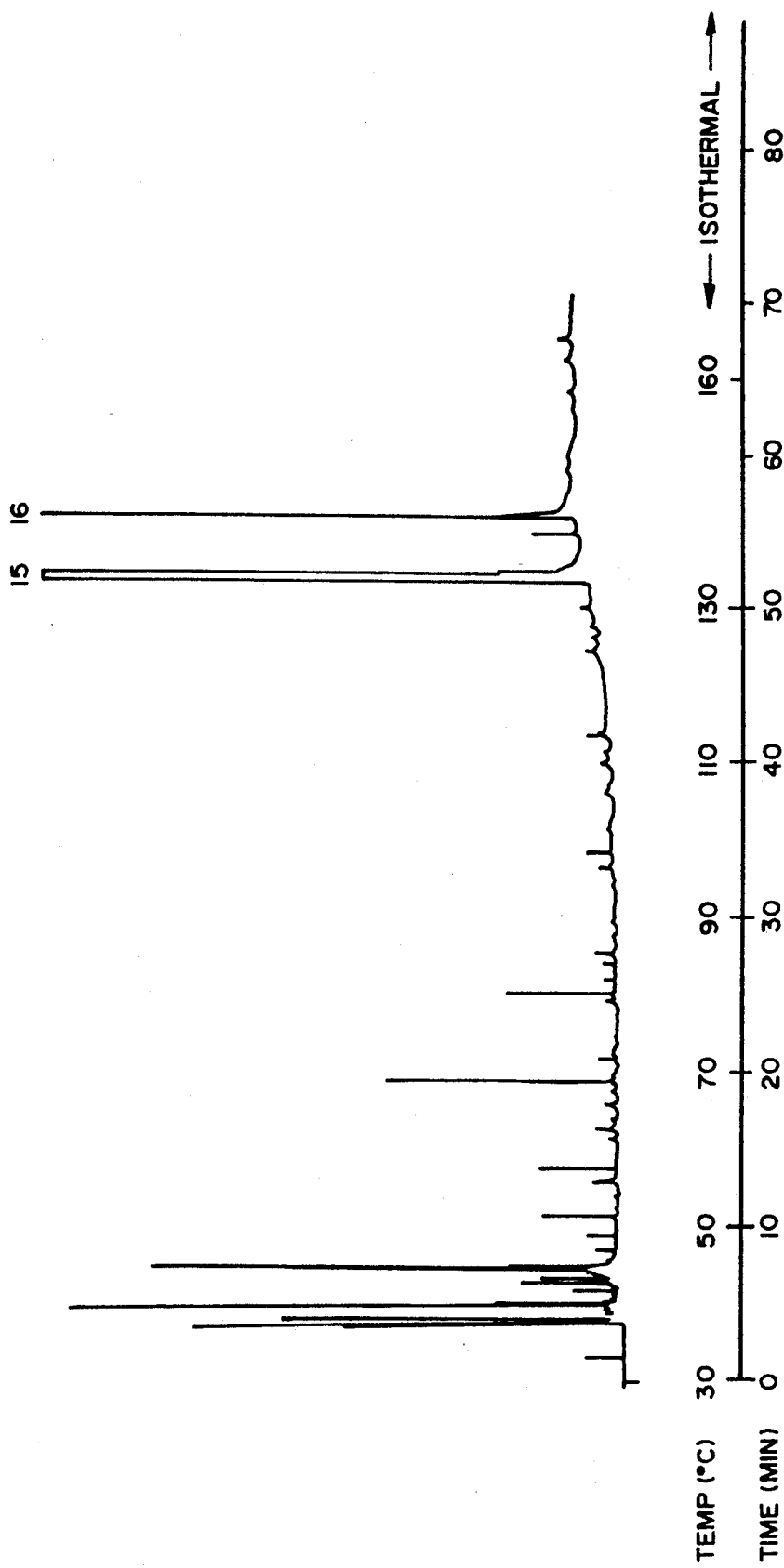

FIG. 3 compares the volatiles from bladder urine of a subordinate male (FIG. 3a), and the volatiles from the preputial gland (FIG. 3b). The sesquiterpenes are conspicuously absent from the analysis of bladder urine (FIG. 3, Table 2), whereas they are predominant constituents in the headspace analysis of the preputial gland. This analysis identifies the preputial glands as being the site of secretion of alpha- and beta-farnesene into the urinary tract. Preputial glands from dominant males contain more E,E-alpha- and E-beta-farnesene per gram of tissue than preputial glands from subordinate males.

Figure 4:
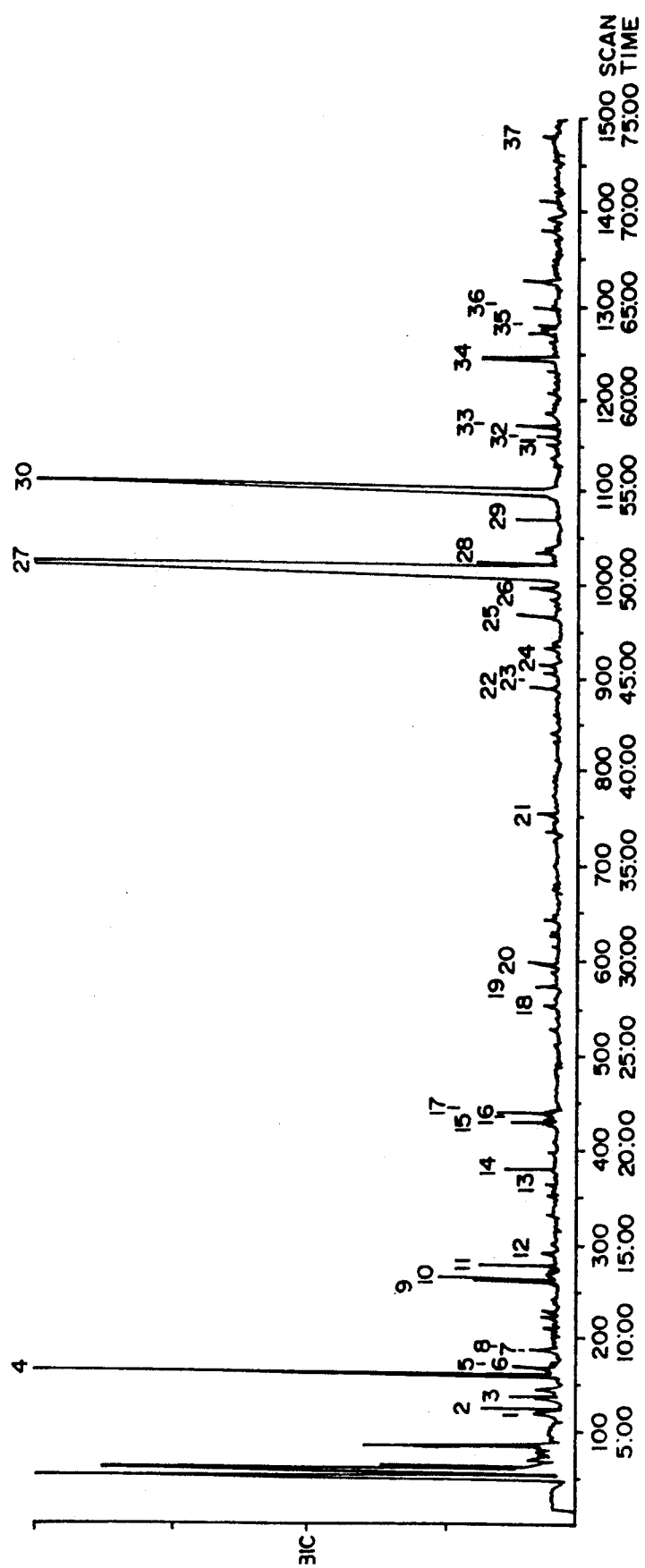
FIG. 4 is a representation of the reconstructed ion current chromatogram of the volatile components of the dominant mouse preputial gland.

A detailed analysis of the headspace components of the preputial glands of dominant mice is initiated in order to identify the constituents present in lower concentrations. FIG. 4 shows a representative reconstructed ion current chromatogram of the preputial headspace. The mass spectral fragmentation patterns allows for the identification of 37 components. Information obtained from 70 eV mass spectra was supplemented with methane and isobutane chemical ionization mass spectral data. Structural identifications, as well as the significant fragment ions and their abundances, are summarized in Table 4.

Of primary interest is the identification of myrcene (peak 9) and ocimene (peak 14) in the preputial gland headspace. The presence of both myrcene and ocimene has been verified by spiking small amounts of these compounds in the preputial gland sebum and observing the peak area enhancement in the corresponding headspace chromatograms. The 10-carbon skeleton of myrcene is incorporated in the structure of E-beta-farnesene and the 10-carbon skeleton of ocimene is found in the structure of E,E-alpha-farnesene.

Figure 5:
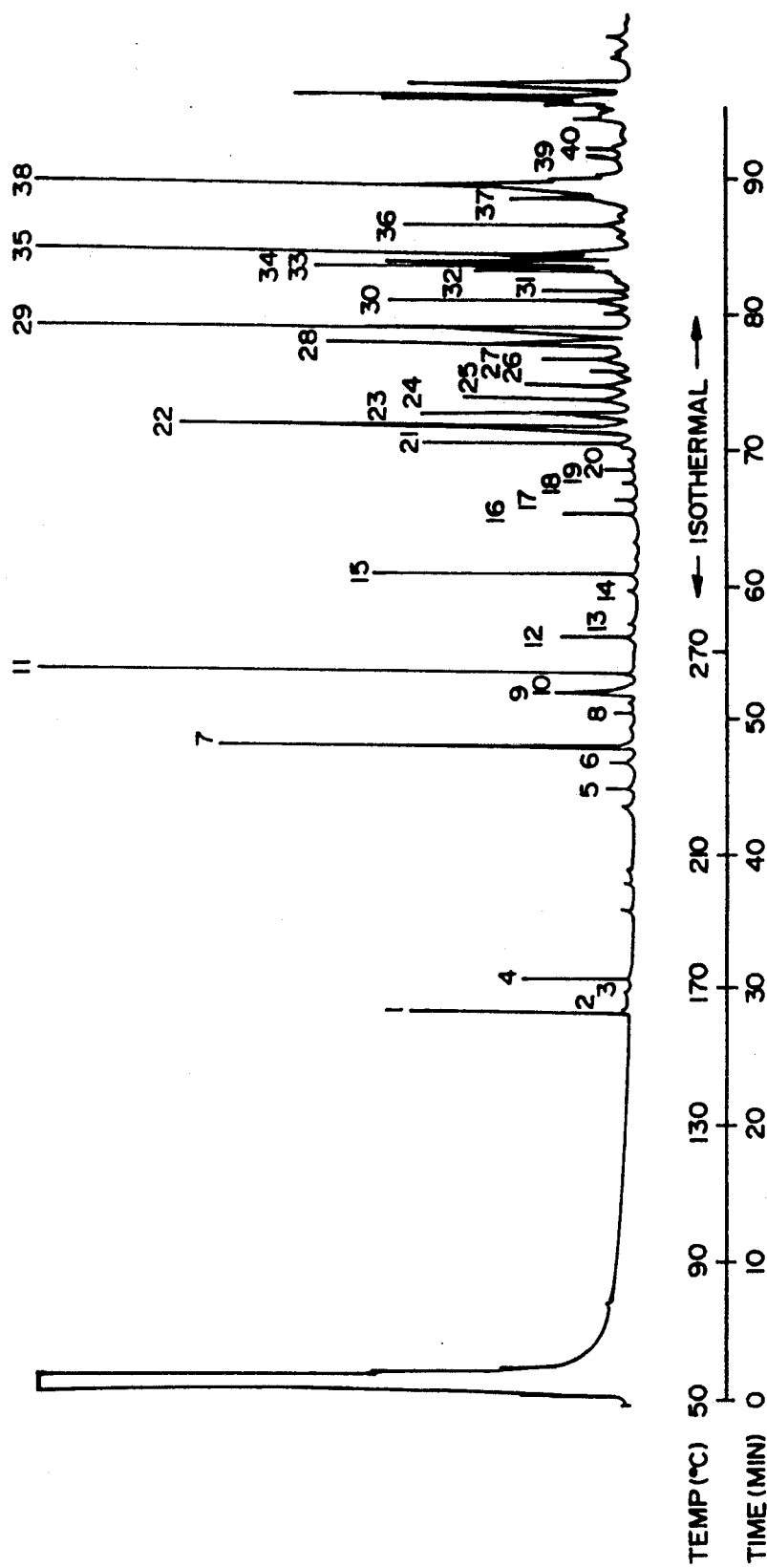
FIG. 5 is a representation of the chromatogram of the semi-volatile components of the dominant mouse preputial gland.

In order to investigate the semi-volatile components of the preputial glands, the sebum contents of two glands are gently squeezed into 5 ml of physiological saline (0.85% NaCl). This solution is extracted with 5 ml pentane. The pentane extract is dried over anhydrous $Na_2SO_4$ and filtered. This solution is then concentrated with a stream of dry nitrogen and analyzed on an SE-30 capillary column (40m×250 um i.d.). A representative chromatogram is presented in FIG. 5. Subsequent GC-MS studies allowed for the identification of 40 components.

The first portion of this chromatogram shows the presence of E,E-alpha-farnesene and E-beta-farnesene. These are the only compounds that are common to both the headspace and semi-volatile chromatograms, indicating a continuity between the two analyses with respect to volatility of the analytes. The next compounds to appear in the chromatogram are long-chain alcohols and their acetates. The remainder of the chromatogram is dominated by a huge series of esters. The structures of many of these esters are compatible with the previous studies involving analysis of the saponified ester fraction. The last third of the chromatogram consists of a family of esters containing tetradecatrienoic acid, which have not previously been reported to be constituents of the preputial gland lipids. These esters comprise a unique group of compounds. Several of the fragments seen in the mass spectra of these esters (m/e—69, 109, and 123) suggest a terpene-type structure and may be structurally related to alpha- and beta-farnesene.

Of fundamental importance was verifying the actual presence of E-beta-farnesene and E,E-alpha-farnesene in the preputial gland extract. Both these sesquiterpenes are known to be Produced by dehydration reactions of farnesol and nerolidol. Since dehydration could occur in the injection port of a gas chromatograph, it is conceivable that nerolidol or farnesol could be present in the preputial gland extract. Dehydration of these alcohols upon injection into the gas chromatograph could account for the observation of the farnesenes in the preputial gland extract. In order to determine if the farnesenes are observed due to the dehydration of an alcohol, the pentane extract of the preputial gland was derivatized with bisilyltrifluoroacetate (BSTFA), a silylation agent. The resulting trimethylsilyl ether derivatives of the alcohols in this mixture would be expected to remain intact during gas chromatographic analysis.

Figure 6:
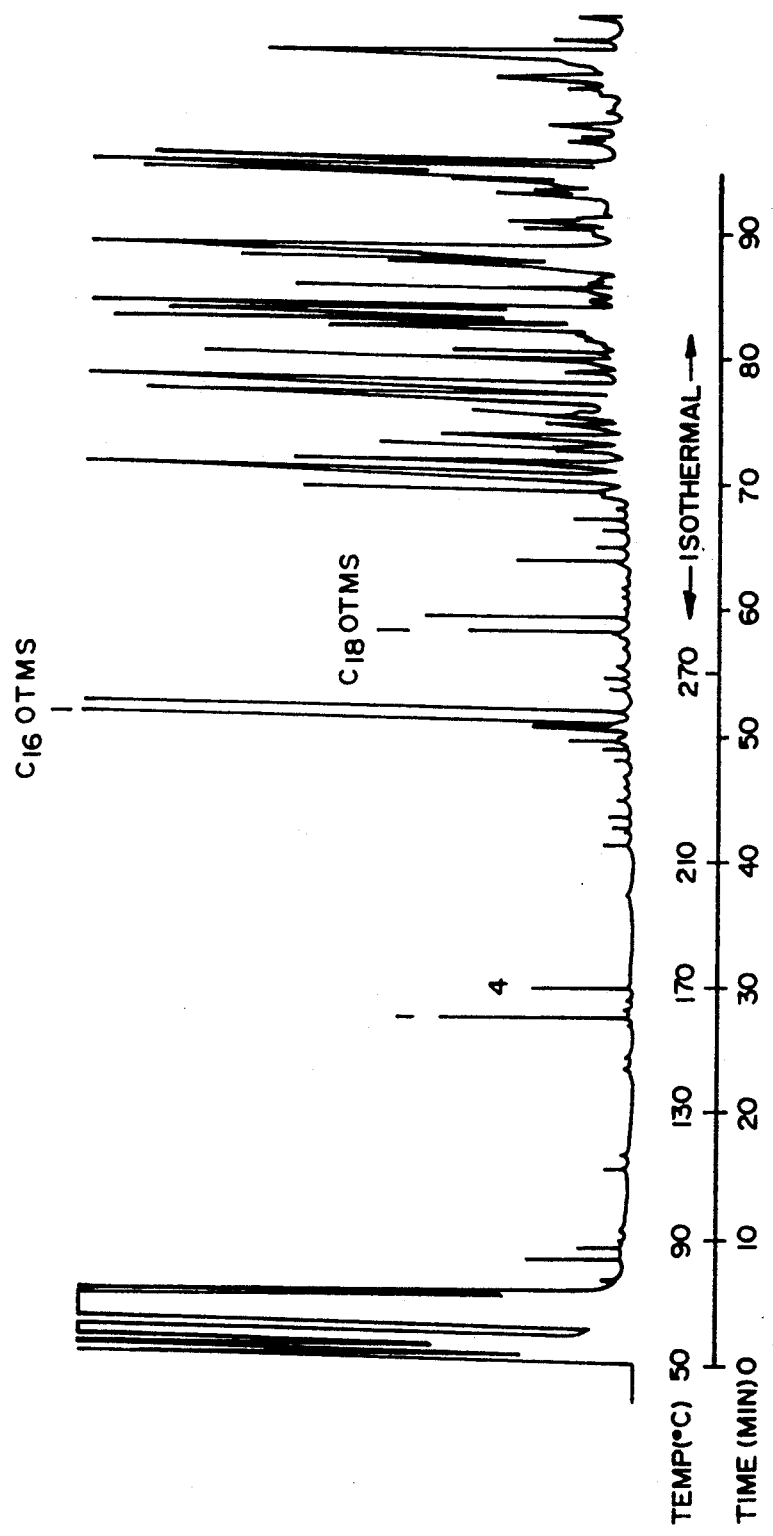
FIG. 6 is a representation of the chromatogram of the pentane extract of the dominant preputial gland derivatized with BSTFA.

FIG. 6 shows a chromatogram of the BSTFA derivatized pentane extract of the preputial gland. E-beta-farnesene (peak 1) and E,E-alpha-farnesene (peak 4) are present in this sample in the same ratio as found in FIG. 5, indicating that these sesquiterpenes are not formed from the dehydration of an alcohol. An interesting feature of this chromatogram is the presence of the trimethylsilyl derivatives of 1-hexadecanol and 1-octadecanol. As expected, the retention times of these derivatized alcohols are increased relative to their underivatized forms. This not only provides additional evidence about the identity of these compounds, but it also verifies that complete derivatization of the sample has taken place.

EXAMPLE II

Synthesis and Isolation of Compounds Used for Structural Verifications a) Acetates Octadecyl and hexadecyl acetates are prepared by reaction of the corresponding alcohols with excess acetyl chloride. To 0.02 moles of alcohol (5.41 g of octadecanol or 4.85 g of hexadecanol) and 50 ml of toluene in a 100-ml round-bottomed flask, 0.04 moles acetyl chloride is slowly added at room temperature over a period of 2 hours, after which the reaction mixture is refluxed for an additional 2 hours The reaction mixture is then washed with two equal volumes of 5% aqueous $Na_2SO_4$. The drying agent is removed through filtration prior to the evaporation of the toluene solvent on a rotary evaporator. Analysis of both crystalline products by capillary gas chromatography reveals a single peak.

b) Esters of Long-Chain Acids

Hexadecyl and tetradecyl decanoates are prepared as follows: to 0.02 moles of alcohol (4.85 g of hexadecanol or 4.57 g of tetradecanol in a 100-ml round-bottomed flask), 0.02 moles of decanoic acid (3.45 g), 3 drops of concentrated sulfuric acid, and 50 ml of toluene were added. The reaction is then washed with two equal volumes of 5% aqueous $Na_2CO_3$ and dried over 5–6 g of anhydrous $Na_2SO_4$. The drying agent is then removed through filtration and the solvent stripped with the aid of a rotary evaporator. Both products are oils which exhibit single peaks when analyzed by capillary gas chromatography.

c) E,E-alpha-Farnesen

Figure 7A:
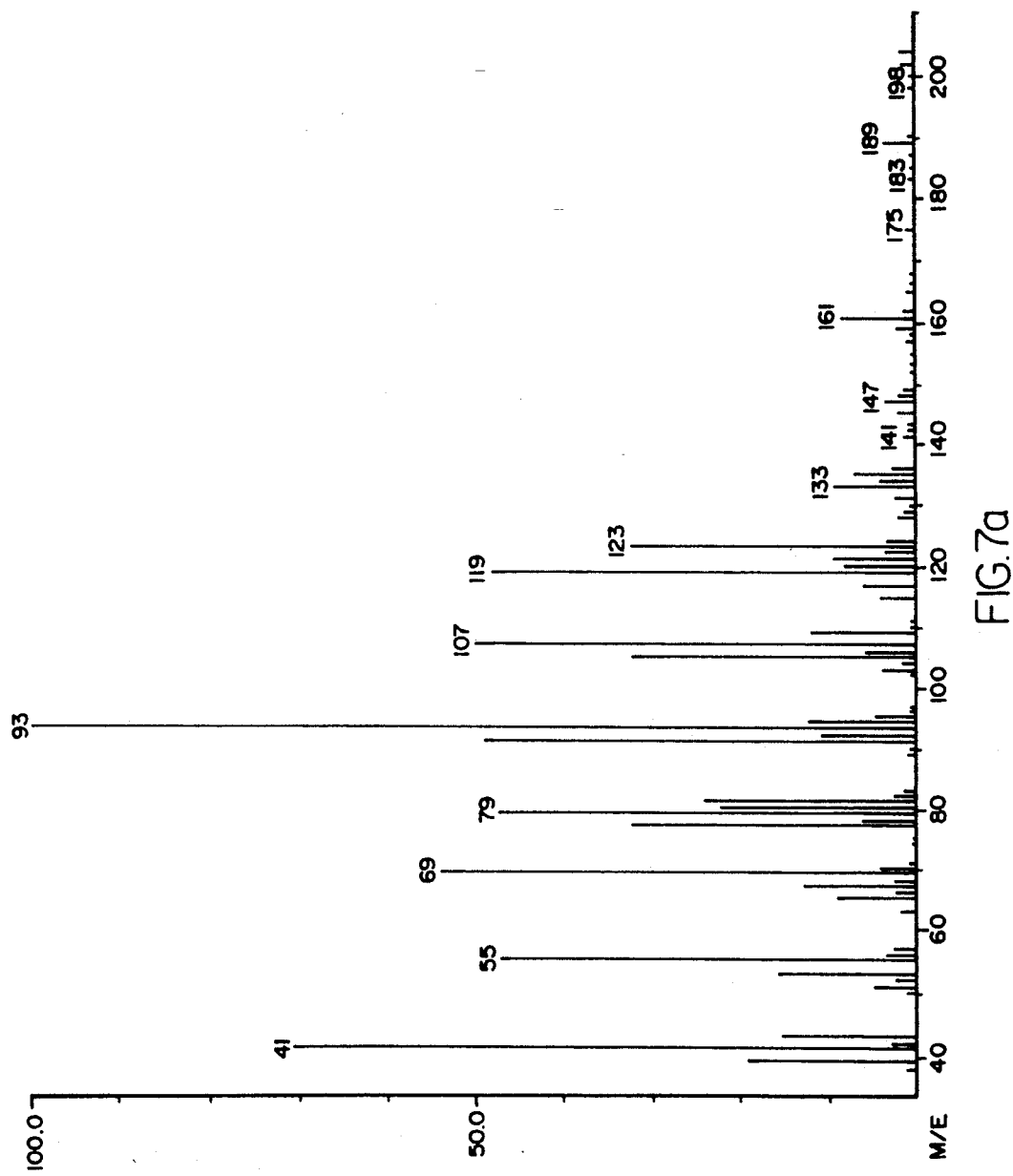
FIG. 7 is a representation of the mass spectrum of synthetic E,E-alpha-farnesene (FIG. 7a) compared to a spectrum of E-E-alpha-farnesene isolated from apples (FIG. 7b).
Figure 7B:
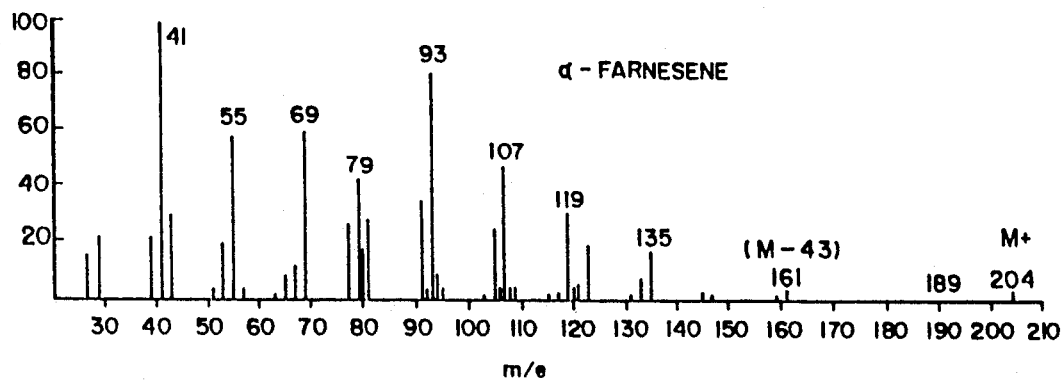

E,E-alpha-farnesene is prepared according to the method of Negishi and Matsushita, Org. Synth., 62: 31, 1984. The first step in this synthesis is the preparation of the intermediate (E)-(2-methyl-1,3-butadienyl)dimethylalane from the zirconocene dichloride-catalyzed addition of trimethylalane to 1-buten-3-yne. The final step in this synthesis involves the reaction of the intermediate with geranyl chloride in the presence of tetrakis(triphenylphosphene)-palladium. Analysis of the product by capillary GC-MS revealed the presence of E,E-alpha-farnesene (67%) and the geranyl chloride (33%) starting material. This product is purified by repetitive preparative gas chromatography on an SE-30 column. The mass spectrum obtained during GC-MS run of this material is shown in FIG. 7. A literature mass spectrum of E,E-alpha-farnesene is included in FIG. 7b for comparison.

d) E-beta-Farnesene

Figure 8B:
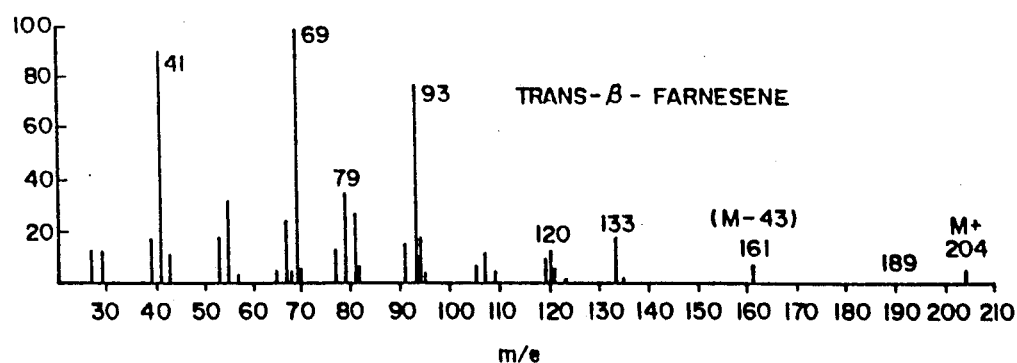
FIG. 8 is a representation of the mass spectrum of E-beta-farnesene isolated from chamomile oil (FIG. 8a) compared to a previously disclosed spectrum of E-beta-farnesene (FIG. 8b) (K. E. Murray, *Austr. J. Chem.* 22: 197, 1969.)
Figure 9A:
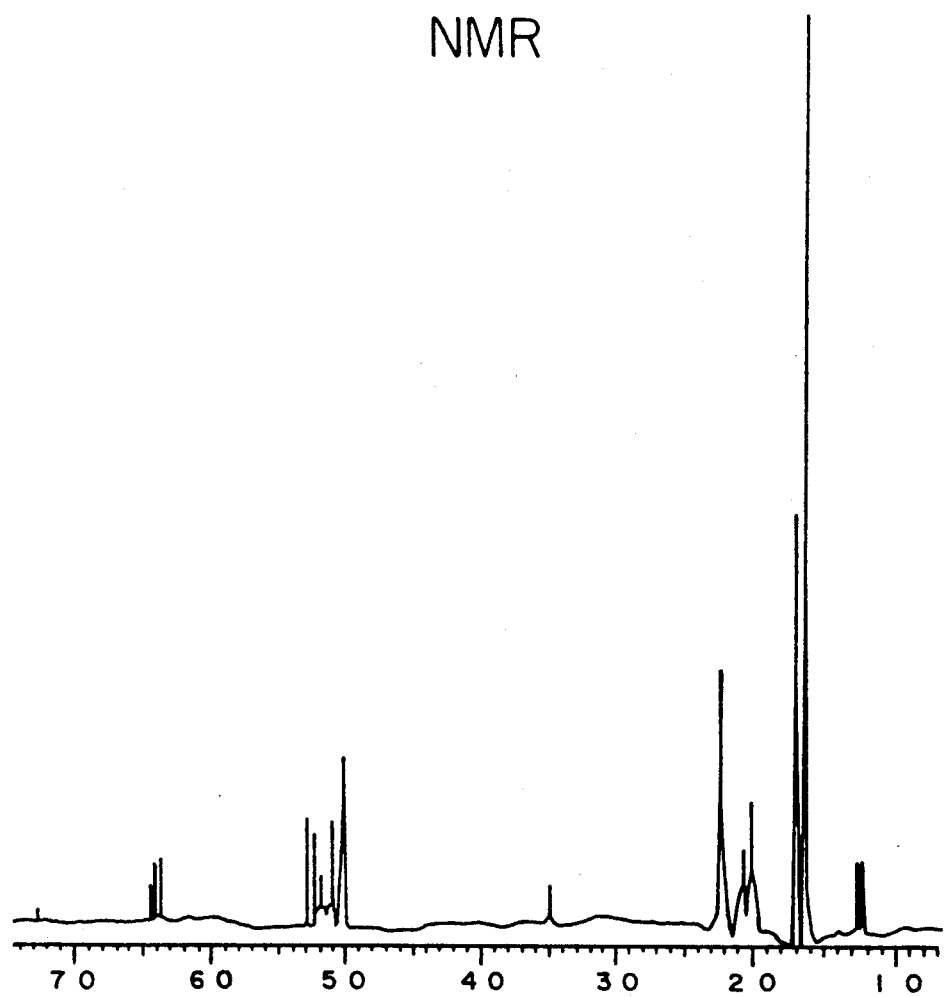
FIG. 9 is a representation of IR and NMR spectra of E-beta-farnesene isolated from chamomile oil (FIG. 9a and 9b) compared to previously disclosed spectra of E-beta-farnesene (FIG. 9c and 9d) (K. E. Murray, supra.)
Figure 9C:
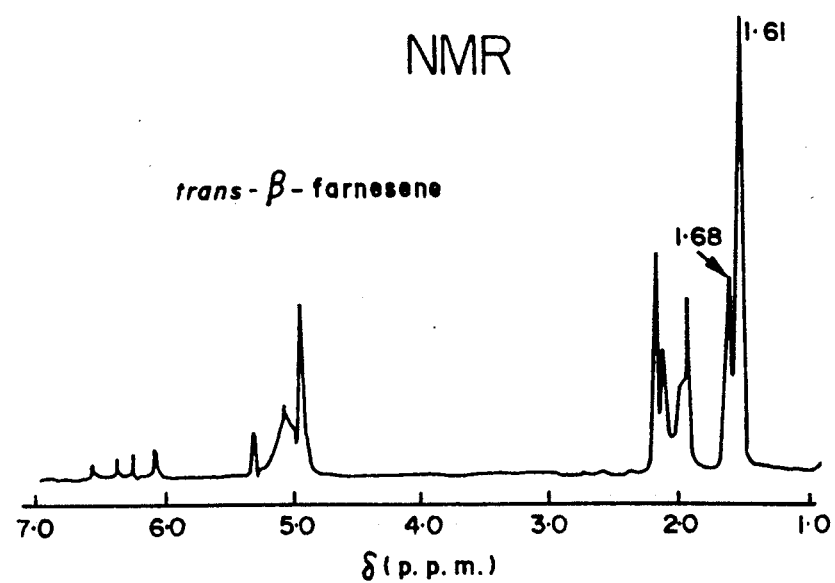
Figure 9B:
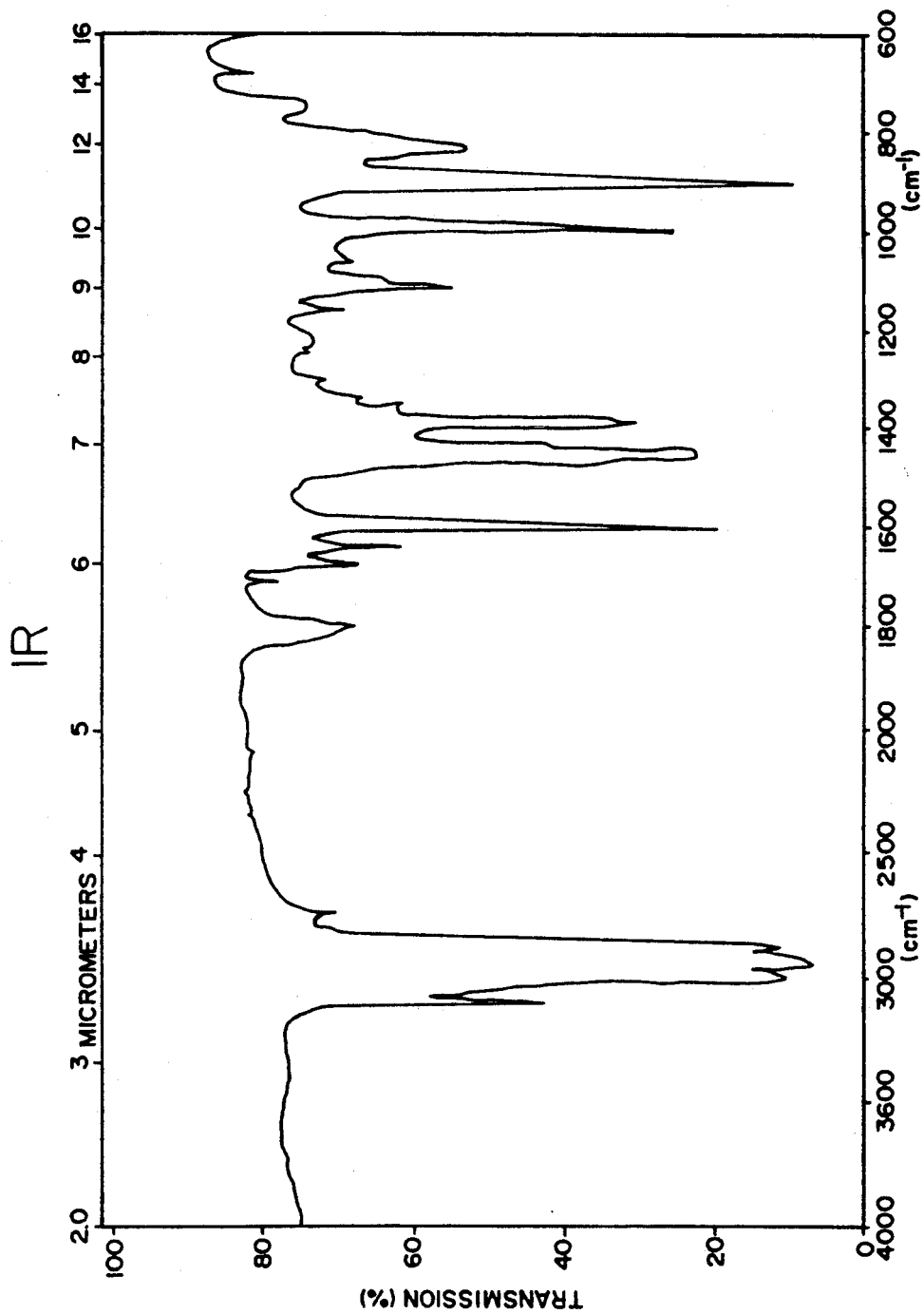

E-beta-farnesene is obtained by chromatographic (HPLC) isolation from chamomile oil. Chamomile oil ("German Extra", Fritzsche Dodge & Olcott, New York, N.Y.) is taken up in diethyl ether (1:1) and extracted twice with equal volumes of 5% aqueous $Na_2CO_3$ to remove the acidic components. The ethereal solution is dried over anhydrous $Na_2SO_4$ and subsequently filtered prior to chromatography. The acidic alumina (Woelm, Eschwege, West Germany) is activated immediately before use by heating at 350° C. for a period of 12 h in order to assure it was activity grade 1. The chromatographic column is a glass tube (32 mm×44 cm) having a 1-liter solvent reservoir and a coarse sintered-glass frit to contain the packing material. The column is packed with a slurry of 362 g acidic alumina in petroleum ether (b. p. 30°-60° C.). A five-ml aliquot of the ethereal chamomile oil is placed on the head of the column and the chromatogram is developed with petroleum ether. Fractions are collected in 100-ml increments and analyzed individually by gas chromatography. E-beta-farnesene started to elute in fraction 8; however, this fraction also contained other components. Gas-chromatographic analysis of fraction 9-17 showed only one peak which was free of contamination by other compounds. Fractions 9-17 were pooled and the solvent removed by a rotary evaporator. GC-MS analysis revealed only one pure component. The mass spectrum obtained for this peak in FIG. 8b. FIG. 9 compares the IR and NMR spectra of the material in the combined fractions with literature spectra of E-beta-farnesene. From the comparisons made in FIGS. 8 and 9, it is clear that the material isolated from chamomile oil is indeed pure E-beta-farnesene.

Co-injection of isolated and synthetic compounds with the preputial gland extract is then performed in order to verify the identifications. Co-elution of the standard compound, as indicated by a relative increase in the peak area, Was used as a criterion for compound verification. In each case, tentative identifications arrived at by mass spectral interpretations were verified for the synthetic samples and the E-beta-farnesene isolated from chamomile oil. Of particular importance was the verification of the trans geometry of both alpha- and beta-farnesene. Additionally, the presence of 1-hexadecanol and 1-octadecanol was confirmed by co-injection of the commercially available alcohols.

EXAMPLE III

Two-Choice Preference Tests

In order to demonstrate the role of alpha- and beta-farnesene as the aversive signal, a series of two-choice preference tests were performed involving the investigatory behavior of male ICR/Alb albino mice.

The test males, 4-6 months old, were housed in groups of four per cage. The dominant male of each cage was Identified and excluded from testing to limit behavioral arena (30×16 cm) with a replaceable floor. Two circular ports (1 cm in diameter), located 3.5 cm above the base of the wall and 180° apart, were used for odor presentation. A glass vial (1×3.5 cm), containing 0.2 ml of a stimulus solution, was fitted into each port so that an animal could sniff the opening without contacting the liquid. Each male (n=9) was tested daily for a 5-min period, following a 5-min period of habitation. Five trials were performed for each male in eight different (see below) experimental situations. The investigatory time was determined as the amount of time the animal spent with a part of its snout in the sample port. The following urines were tested relative to water: [1] female urine; [2] female urine containing alpha- and beta-farnesene; [3] dominant male urine; [4] subordinate male urine; [5] subordinate male bladder urine without alpha- and beta-farnesene; [6] subordinate bladder urine containing synthetic alpha- and beta-farnesene. Additional experiments tested bladder urine without alpha- and beta-farnesene [7] and bladder urine containing alpha- and beta-farnesene [8] relative to water containing alpha- and beta-farnesene. The synthetic compounds were present in the samples at concentrations simulating their content in dominant male urine (about 5 p.p.m., v/v, each).

Table 7 shows the total time that the animals spent investigating the sample ports during the 5-minute test for each of the eight experimental conditions. The results clearly indicate the males' preference for female urine, subordinate urine, and male bladder urine (conditions 1, 4, and 5) when compared to water. Additionally, the tested animals exhibited significantly lower sniffing activity in the presence of dominant male urine when compared to urine from submissive males. The most dramatic decrease in investigative activity was observed when any sample contained alpha- and beta-farnesene. Both female urine and male bladder urine, when spiked with these compounds (conditions 2 and 6) are less preferable to tested males when compared to corresponding trials with unspiked urine (conditions 1 and 5). Addition of the sesquiterpenes into these samples decreased the total motor activity of animals in the test chamber by approximately 50%. An extremely low motor activity was observed when the test animals were simultaneously exposed to two samples containing the farnesene; in condition 8, the sniffing activity of animals dropped 62.5% compared to the testing condition (5) employing the bladder urine and water which did not contain the farnesenes.

TABLE 1

| Volatile compounds in the urine of ICR/Alb male mice. | | |
|---|---|---|
| Class of compounds | Structure | Peak number |
| Dihydrofurans | m.w. 126* | 1 |
| | m.w. 126* | 2 |
| | m.w. 126* | 3 |
| Ketones | 2-heptanone | 4 |
| | 5-heptene-2-one | 7 |
| | 4-heptene-2-one | 8 |
| | 3-heptene-2-one | 9 |
| | 6-methyl-6-hepten-3-one | 10 |
| | 6-methyl-5-hepten-3-one | 11 |
| | acetophenone | 14 |
| Acetates | n-pentyl acetate | 5 |
| | 2-penten-1-yl acetate | 6 |
| Dehydro-exo-brevicomin | | 12 |
| 2-(sec-butyl)-4,5-dihydrothiazole | | 13 |
| Sesquiterpenes | β-farnesene | 15 |
| | α-farnesene | 16 |

*presumed isomeric cyclic vinyl ethers unique to the mouse [29]; dehydration products of a known 5,5-dimethyl-2-ethyltetrahydrofuran-2-ol.

TABLE 2

Mean (± S.E.M.) value of peak areas for four selected volatile compounds of male mouse urine after hormonal manipulations and social rank test.

| | Peak area in arbitrary units | | | |
|---|---|---|---|---|
| | β-farnesene | α-farnesene | dehydro-exo-brevicomin | 2-(sec-butyl)-4,5-dihydrothiazole |
| Type of sample | Peak number | | | |
| | [15] | [16] | [12] | [13] |
| EXCRETED URINE | | | | |
| Immature | 0.0 | 0.0 | 0.0 | 0.0 |
| Intact | 12.8 (1.3)[a] | 5.2 (0.4)[a] | 4.2 (0.4)[a] | 18.6 (1.9)[a,c] |
| Castrated (CD) | 3.1 (1.3)[b] | 1.2 (0.4)[b] | 0.0 | 0.0 |
| CD + testosterone | 0.6 (0.0)[c] | 0.3 (0.0)[b] | 2.1 (0.3)[b] | 0.4 (0.0)[b] |
| BLADDER URINE | | | | |
| Dominant | 0.0 | 0.0 | 7.9 (0.5)[c] | 25.1 (2.3)[a] |
| Subordinate | 0.0 | 0.0 | 6.3 (0.7)[c] | 11.6 (1.9)[c] |

The means not marked by the letters (a, b, c) are significantly different at the 0.02 level (ANOVA).

TABLE 3

Body weights (g) and relative organ weights (mg/100 g) of mice experiencing repeated (10-day period) victory or defeat. Body and listed organs were weighed 7 days after the last fight took place.

| | CONTROL* (n = 10) | SUBORDINATE (n = 12) | DOMINANT (n = 12) | ANALYSIS OF VARIANCE |
|---|---|---|---|---|
| Body | 39.7 (1.3) | 37.4 (0.9) | 37.5 (0.7) | NS |
| Paired testes | 777.1 (23.7) | 637.4 (52.1)[a] | 778.2 (37.1) | $p < 0.05$ |
| Paired seminal vesicles and coagulating glands | 849.7 (25.7) | 888.0 (37.6) | 938.8 (46.5) | NS |
| Paired preputial glands | 285.9 (20.6)[a] | 332.1 (23.1)[b] | 434.6 (16.5)[c] | $p < 0.001$ |
| Paired adrenal glands | 8.9 (0.7) | 14.4 (0.9)[a] | 8.6 (0.9) | $p < 0.001$ |

*Socially inexperienced singly-caged males that were sacrificed at the age of 6 months
( ) ± S.E.M.

TABLE 4

Mass-spectral data and identifications of preputial gland volatiles.

| Peak # | Identification | Significant m/e (Relative Intensity) |
|---|---|---|
| 1. | Toluene | 92(50), 91(100) |
| 2. | 2,2,6-Trimethylheptane | 99(18), 85(20), 71(40), 57(100), 56(47), 43(29) |
| 3. | (Me$_2$SiO)$_4$ | 281(100), 207(13), 198(19), 191(19), 133(25), 73(15), 71(33) |
| 4. | 2,2-Dichloro-1,1-difluoro-1-methoxyethane | 135(6), 133(8), 98(9), 95(6), 87(3), 85(16), 83(26), 81(100) |
| 5. | 5-Methyl-3-hexanone | 114(8), 85(47), 56(100) |
| 6. | Decane | 142(5), 113(15), 95(9), 85(28), 71(76), 57(71), 43(100) |
| 7. | Ethylbenzene | 106(85), 91(100) |
| 8. | p-Xylene | 106(61), 91(100) |
| 9. | Myrcene | 136(4), 121(7), 93(100), 79(18), 69(71), 53(12), 41(72) |
| 10. | Undecane | 141(1), 127(3), 85(31), 71(45), 57(80), 43(100), |
| 11. | (Me$_2$SiO)$_5$ | 267(100), 251(15), 193(12), 73(100) |
| 12. | A C$_3$ benzene | 120(29), 105(100) |
| 13. | A C$_3$ benzene | 120(37), 105(100) |
| 14. | Ocimene | 136(7), 121(19), 105(23), 93(100), 79(57), 77(39) |
| 15. | Dodecane | 170(3), 127(3), 113(3), 99(6), 85(31), 71(50), 57(84), 43(100) |
| 16. | A C$_3$ benzene | 120(39), 105(100) |
| 17. | 6-Methyl-5-hepten-2-one | 126(5), 111(18), 108(34), 93(10), 69(26), 58(21), 55(30), 43(100) |
| 18. | (Me$_2$SiO)$_6$ | 341(100), 325(39), 207(15), 147(31), 119(25), 73(97) |
| 19. | Nonanal | 114(8), 98(19), 81(17), 68(26), 57(53), 44(100) |
| 20. | Tridecane | 184(4), 113(10), 106(15), 97(13), 85(39), 71(52), 57(98), 43(100) |
| 21. | Tetradecane | 198(4), 169(5), 141(8), 99(6), 85(49), 71(52), 57(82), 43(100) |
| 22. | Naphthalene | 128(100) |
| 23. | Pentadecane | 127(9), 113(10), 99(12), 85(34), 71(51), 57(66), 43(100) |
| 24. | Like E-beta-farnesene | 161(10), 133(13), 120(14), 93(25), 69(100), 41(67) |
| 25. | Like E-beta-farnesene | 161(22), 133(36), 120(26), 93(66), 69(100), 41(67) |
| 26. | A polysiloxane | 327(14), 281(56), 221(44), 147(53), 73(100), 43(40) |
| 27. | E-beta-farnesene | 204(2), 161(16), 133(30), 120(18), 93(59), 69(100), 41(60) |
| 28. | Unknown structure | 91(43), 67(42), 57(44), 55(39), 43(55), 41(100) |
| 29. | Like alpha-farnesene | 161(9), 135(14), 119(74), 107(35), 105(35), 93(97), 91(41), 79(31), 69(42), 57(51), 55(50), 43(100), 41(57) |
| 30. | Alpha-farnesene | 161(8), 123(33), 119(48), 107(50), 93(100), 91(49), 79(47), 69(54), 55(47), 41(71) |
| 31. | Geranylacetone | 151(13), 136(10), 125(7), 107(11), 69(27), 43(100) |
| 32. | Heptadecane | 141(11), 113(11), 85(49), 71(53), 57(100) |
| 33. | A polysiloxane | 341(46), 281(47), 221(72), |

TABLE 4-continued

Mass-spectral data and identifications of preputial gland volatiles.

| Peak # | Identification | Significant m/e (Relative Intensity) |
|---|---|---|
| | | 147(75), 73(100), 43(77) |
| 34. | An alcohol of molecular weight equal to 222. Not farnesol or nerolidol | 204(38), 135(100), 107(93), 105(36), 93(47), 91(47), 55(32), 43(65), 41(58) |
| 35. | A branched alkane | 155(7), 113(8), 85(18), 71(28), 57(43), 56(84), 43(100), 41(57) |
| 36. | A branched alkene | 97(18), 83(19), 69(26), 57(28), 55(32), 43(100), 41(66) |
| 37. | 2-Phenyl dodecane | 246(11), 149(11), 105(100), 70(20), 56(33), 43(86) |

TABLE 5

Mass-spectral data and identifications of preputial gland semivolatiles.

| Peak # | Identification | Significant m/e (Relative Intensity) |
|---|---|---|
| 1. | E-beta-Farnesene | 204(1), 161(12), 133(25), 120(16), 93(52), 69(100), 41(82) |
| 2. | Butylated hydroxytoluene | 220(26), 205(100), 161(51) |
| 3. | Butylated hydroxytoluene | 220(28), 205(100), 161(11) |
| 4. | E,E-alpha-Farnesene | 161(9), 123(37), 119(48), 107(58), 93(100), 91(54), 79(47), 69(56), 55(48), 41(77) |
| 5. | A tetradecenyl acetate | 254(4), 194(12), 166(10), 96(44), 95(57), 82(71), 81(62), 67(76), 43(100) |
| 6. | Tetradecyl acetate | 168(9), 111(20), 97(37), 83(39), 69(32), 61(22), 55(34), 43(100) |
| 7. | 1-Hexadecanol | 196(5), 97(54), 83(74), 69(71), 57(90), 55(93), 43(97), 41(100) |
| 8. | A hexadecenyl acetate | 222(7), 194(3), 95(51), 82(61), 67(57), 43(100) |
| 9. | A hexadecenyl acetate | 222(12), 195(4), 95(63), 82(78), 67(75), 43(100) |
| 10. | A hexadecenyl acetate | 223(7), 96(53), 82(78), 81(63), 55(72), 43(100) |
| 11. | Hexadecyl acetate | 224(1), 196(5), 111(20), 97(39), 83(47), 69(40), 61(32), 55(41), 43(100) |
| 12. | 1-Octadecanol | 125(13), 111(24), 97(47), 83(53), 70(69), 61(31), 57(84), 43(100) |
| 13. | An octadecen-1-ol | 141(8), 109(15), 97(39), 82(67), 69(47), 57(90), 43(100) |
| 14. | An octadecenyl acetate | 251(10), 207(8), 138(19), 123(24), 110(29), 96(58), 95(57), 82(71), 81(58), 67(62), 55(71), 43(100) |
| 15. | Octadecyl acetate | 225(3), 97(34), 83(41), 69(36), 61(34), 55(39), 43(100) |
| 16. | Ester: $C_8$ acid, $C_{14}$ alcohol (unsaturated) | 194(21), 166(17), 138(19), 127(49), 109(28), 96(62), 95(66), 82(100), 67(72) |
| 17. | Ester: $C_8$ acid, $C_{14}$ alcohol (saturated) | 196(6), 173(31), 155(13), 145(100), 127(30), 97(27), 83(32), 57(62), 43(69) |
| 17. | Ester: $C_{10}$ acid, $C_{12}$ alcohol (saturated) | 196(6), 173(31), 155(13), 145(100), 127(30), 97(27), 83(32), 57(62), 43(69) |
| 18. | A tetradecenyl benzoate | 194(17), 163(25), 149(44), 123(45), 105(100), 95(55), 82(75), 67(64) |
| 19. | Ester: $C_9$ acid, $C_{14}$ alcohol (unsaturated) | 194(21), 187(16), 166(16), 159(30), 149(30), 141(39), 96(71), 82(100), 67(72), 55(92), 43(76), 41(74) |
| 20. | Ester: $C_9$ acid, $C_{14}$ alcohol (saturated) | 267(3), 242(4), 197(7), 173(28), 159(96), 141(26), 71(53), 57(80), 55(65), 43(100) |
| 21. | Ester: $C_{10}$ acid, $C_{14}$ alcohol (unsaturated) | 194(20), 173(9), 166(20), 155(12), 137(21), 124(16), 109(24), 96(63), 95(66), 82(100), 55(64), 43(66) |
| 22. | Ester: $C_{10}$ acid, $C_{14}$ alcohol (unsaturated) | 194(21), 173(7), 166(23), 155(33), 138(21), 124(18), 109(23), 96(68), 95(59), 82(100), 67(60), 55(62) |
| 23. | Ester: $C_{10}$ acid, $C_{14}$ alcohol (saturated) | 196(7), 173(100), 168(3), 155(23), 145(22), 129(8), 111(14), 97(25), 83(27), 69(26), 57(38), 43(45) |
| 24. | Ester: $C_{11}$ acid, $C_{14}$ alcohol (unsaturated) | 194(15), 187(6), 166(16), 151(10), 138(18), 123(16), 109(28), 95(71), 82(100), 67(67), 55(80) |
| 25. | Ester: $C_{11}$ acid, $C_{14}$ alcohol (saturated) | 241(3), 196(6), 187(100), 173(18), 155(11), 129(17), 111(19), 97(36), 83(46), 69(44), 57(69), 43(67) |
| 26. | Ester: $C_{10}$ acid $C_{15}$ alcohol (saturated) | 225(3), 211(3), 197(4), 173(100), 159(61), 155(22), 141(16), 129(12), 111(22), 97(38), 83(41), 71(41), 57(62), 43(75) |
| 26. | Ester: $C_9$ acid $C_{16}$ alcohol (saturated) | 225(3), 211(3), 197(4), 173(100), 159(61), 155(22), 141(16), 129(12), 111(22), 97(38), 83(41), 71(41), 57(62), 43(75) |
| 27. | Ester: $C_{10}$ acid $C_{16}$ alcohol (unsaturated) | 222(18), 194(8), 173(16), 155(17), 149(38), 137(16), 123(15), 109(28), 95(64) 82(100), 67(65), 55(64), 43(66) |
| 28. | Ester: $C_{10}$ acid, $C_{16}$ alcohol (saturated) | 224(5), 222(7), 173(100), 155(16), 129(15), 111(19), 97(37), 83(45), 82(45), 69(47), 55(53), 43(62) |
| 29. | Ester: $C_{10}$ acid, $C_{16}$ alcohol (saturated) | 224(4), 173(100), 155(18), 129(7), 111(11), 97(19), 83(21), 69(20), 57(27), 43(30) |
| 30. | Ester: $C_{11}$ acid, $C_{16}$ alcohol (saturated) | 270(2), 224(4), 187(100), 173(11), 169(8), 139(12), 129(17), 111(16), 97(31), 83(33), 69(35), 57(59), 43(50) |
| 31. | Ester: $C_{11}$ acid, $C_{16}$ alcohol (saturated) | 270(2), 224(4), 187(100), 173(5), 169(19), 143(6), 111(13), 97(26), 83(31), 69(29), 57(43), 43(54) |
| 32. | Ester: $C_{14}$ trienoic acid, $C_{14}$ alcohol (unsaturated) | 390(12), 237(6), 195(13), 177(38), 123(38), 109(70), 69(100) |
| 33. | Ester: $C_{12}$ acid, $C_{16}$ alcohol (saturated) | 270(2), 224(4), 201(100), 183(11), 111(11), 97(20), 83(22), 71(19), 57(36), 43(41) |
| 34. | Ester: $C_{14}$ trienoic acid, $C_{14}$ alcohol (saturated) | 392(10), 237(4), 195(11), 177(38), 123(39), 109(78), 69(100) |
| 35. | Ester: $C_{12}$ acid, $C_{16}$ alcohol (saturated) | 270(3), 224(4), 201(100), 183(16), 111(14), 97(27), 83(29), 69(25), 57(40), 43(45) |
| 36. | Ester: $C_{13}$ acid, $C_{16}$ alcohol (saturated) | 224(4), 215(100), 201(16), 111(15), 97(30), 83(33), 71(28), 57(53), 43(46) |
| 37. | Ester: $C_{14}$ trienoic acid, $C_{16}$ alcohol (saturated) | 420(15), 247(5), 208(11), 195(11), 177(44), 122(20), 109(79), 69(100) |
| 38. | Ester: $C_{14}$ trienoic acid, | 420(11), 237(6), 195(15), |

TABLE 5-continued

Mass-spectral data and identifications of preputial gland semivolatiles.

| Peak # | Identification | Significant m/e (Relative Intensity) |
|---|---|---|
| | $C_{16}$ alcohol (saturated) | 177(46), 123(40), 109(92), 69(100) |
| 39. | Ester: $C_{14}$ trienoic acid, $C_{17}$ alcohol (saturated) | 434(13), 237(4), 195(12), 177(46), 123(37), 109(80), 69(100) |
| 40. | Ester: $C_{14}$ trienoic acid, $C_{17}$ alcohol (saturated) | 434(13), 195(21), 177(54), 123(46), 109(97), 69(100) |

TABLE 6

Composition of alkyl acetates (weight %) in the preputial glands of male mice.

| Compound | (present) ICR males | (spener) CD-1 males | (spener) C-57 males |
|---|---|---|---|
| Tetradecenyl acetate | 1.0 | 0.4 | 4.2 |
| Tetradecyl acetate | 1.0 | 0.4 | 1.5 |
| Hexadecenyl acetate | 14.8 | 9.6 | 15.6 |
| Hexadecyl acetate | 78.5 | 75.2 | 68.0 |
| Octadecenyl acetate | 1.0 | 1.9 | 1.7 |
| Octadecyl acetate | 3.7 | 4.8 | 4.4 |

TABLE 7

Response of male mice to the odor of various urine types and water presented with or without synthetic compounds: α- and β-farnesene.

| Experiment | Total investigatory time (s) | Total activity (s) | Decrease of activity (%) | # of males preferring urine over water |
|---|---|---|---|---|
| A. 1. Female urine | 1917 a** | | | 9 |
| Water | 860 b | 2777 | 0.0 | 0 |
| 2. Female urine and α- + β-farnesene | 755 b* | | | 3 |
| Water | 567 c | 1322 | 52.4 | 0 |
| B. 3. Dominant urine | 355 a** | | 26.8 | 0 |
| Water | 641 b | 966 | | 9 |
| 4. Subordinate urine | 868 b** | | | 8 |
| Water | 453 a | 1321 | 0.0 | 0 |
| C. 5. Bladder urine | 1000 a** | | | 8 |
| Water | 573 b | 1573 | 0.0 | 0 |
| 6. Bladder urine and α- and β-farnesene | 288 d** | | | 1 |
| Water | 636 b | 924 | 41.3 | 8 |
| 7. Bladder urine | 930 a* | | | 6 |
| Water and α- + β-farnesene | 427 c | 1357 | 13.7 | 0 |
| 8. Bladder urine and α- + β-farnesene | 393 c* | | | 2 |
| Water and α- + β-farnesene | 247 d | 640 | 59.3 | 0 |

Statistical comparisons were made using t-Test for small samples (Paired t-Test) (30).
Those values not marked with the same letters (a, b, c, d) within the experimental group A, B, or C, are significantly different at the 0.05 level.
Asterisks are related to two-choice test comparion within group 1-8; *significant at the level 0.01; **significant at the level 0.001.

We claim:

1. A method for inhibiting colonization by a mouse population in a given area which comprises treating said area with a composition comprising an aversion signalling effective amount of an E,E-alpha-farnesene or an E-beta-farnesene or a derivative of said α-farnesene or said β-farnesene to discourage territorial and sexual investigation by male mice, said pheromone or derivative thereof being present in an amount from about 0.01% to about 95% of the total composition, said pheromone being used in a form other than male mouse urine.

2. The method of claim 1 wherein said pheromone is present in a concentration of about 1 ppm to about 50 ppm (v/v).

3. A method of inhibiting territorial and sexual investigation by a male mouse into a given area comprising treating said area with a composition comprising an aversion signalling effective amount of E,E-alpha-farnesene or E-beta-farnesene present in from about 0.01% to about 95% of said composition, wherein said composition is not male mouse urine.

* * * * *

UNITED STATES PATENT AND TRADEMARK OFFICE
CERTIFICATE OF CORRECTION

PATENT NO. : 5,252,326
DATED : October 12, 1993
INVENTOR(S) : Novotny, et al.

It is certified that error appears in the above-indentified patent and that said Letters Patent is hereby corrected as shown below:

Column 1, line 54: "interamale" should read --intermale--

Column 5, line 9: after "1a)" insert --and--

Column 10, line 47: "dihydro thiazole" should read --dihydrothiazole--

Column 11, line 61 : "Produced" should read --produced--

Column 13, line 66: after "behavioral" insert --variation. Each remaining animal was tested in a cylindrical--

Column 13, line 65: "Identified" should read --identified--

Column 15, line 48, Table 4: "56" should read --57--

Signed and Sealed this

Thirteenth Day of September, 1994

Attest:

*Attesting Officer*

BRUCE LEHMAN

*Commissioner of Patents and Trademarks*